(12) United States Patent
Qian

(10) Patent No.: US 11,118,065 B2
(45) Date of Patent: *Sep. 14, 2021

(54) FLUORENYLAMINOKETONE PHOTOINITIATOR, PREPARATION METHOD THEREOF, AND UV PHOTOCURABLE COMPOSITION CONTAINING SAME

(71) Applicants: CHANGZHOU TRONLY ADVANCED ELECTRONIC MATERIALS CO., LTD., Changzhou (CN); CHANGZHOU TRONLY NEW ELECTRONIC MATERIALS CO., LTD., Changzhou (CN)

(72) Inventor: Xiaochun Qian, Changzhou (CN)

(73) Assignee: CHANGZHOU TRONLY ADVANCED ELECTRONIC MATERIALS CO., LTD., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/485,724

(22) PCT Filed: Feb. 11, 2018

(86) PCT No.: PCT/CN2018/076209
§ 371 (c)(1),
(2) Date: Aug. 13, 2019

(87) PCT Pub. No.: WO2018/149370
PCT Pub. Date: Aug. 23, 2018

(65) Prior Publication Data
US 2020/0002544 A1 Jan. 2, 2020

(30) Foreign Application Priority Data

Feb. 17, 2017 (CN) .......................... 201710088234.X
May 18, 2017 (CN) .......................... 201710353951.0

(51) Int. Cl.
C08F 2/46 (2006.01)
C08F 2/50 (2006.01)
C08G 61/04 (2006.01)
C09D 4/00 (2006.01)
C07C 45/41 (2006.01)
C07C 45/63 (2006.01)
C07C 221/00 (2006.01)
C07C 225/18 (2006.01)
C07D 265/30 (2006.01)
C07D 295/135 (2006.01)
C09D 11/037 (2014.01)
(Continued)

(52) U.S. Cl.
CPC ................ C09D 4/00 (2013.01); C07C 45/41 (2013.01); C07C 45/63 (2013.01); C07C 221/00 (2013.01); C07C 225/18 (2013.01); C07D 265/30 (2013.01); C07D 295/135 (2013.01); C09D 11/037 (2013.01); C09D 11/101 (2013.01); C09D 11/107 (2013.01); G03F 7/0295 (2013.01); C07C 2603/18 (2017.05); C08K 5/17 (2013.01); C08K 5/3435 (2013.01); C08K 5/357 (2013.01)

(58) Field of Classification Search
CPC ... C09D 11/101; C09D 11/037; C09D 11/107; C09D 4/00; C07D 211/06; C07D 295/135; C07D 401/10; C07D 413/10; C07D 265/30; C08K 5/357; C08K 5/3435; C08K 5/17; C07C 45/46; C07C 45/41; C07C 45/63; C07C 45/81; C07C 45/78; C07C 45/61; C07C 225/18; C07C 49/778; C07C 2603/18; G03F 7/0295
USPC ...................... 522/6, 189, 184, 71, 1; 520/1
See application file for complete search history.

(56) References Cited

U.S. PATENT DOCUMENTS 4,374,984 A 2/1983 Eichler et al.
4,533,670 A 8/1985 Robertson
(Continued)

FOREIGN PATENT DOCUMENTS

CN 101724099 A 6/2010
CN 102267887 A 12/2011
(Continued)

OTHER PUBLICATIONS

Cha et al, KR 1020140144809 Machine Translation, Dec. 22, 2014 (Year: 2014).*

(Continued)

Primary Examiner — Jessica Whiteley
(74) Attorney, Agent, or Firm — Pillsbury Winthrop Shaw Pittman LLP

(57) ABSTRACT

A fluorenylaminoketone photoinitiator, a preparation method thereof, and a UV photocurable composition containing same. The photoinitiator has a compound having a structure as shown in general formula (I) or a derivative compound thereof. The fluorenylaminoketone photoinitiator may effectively improve the solubility of traditional photoinitiators and reduce the use of micromolecular active diluents, and may also have high sensitivity and good deep-layer curing. It has very good promotion effect on popularization and application of photocurable compositions, particularly colored ink systems, in the field of photocuring. A UV photocurable composition containing such a fluorenylaminoketone photoinitiator can have an advantage in terms of high sensitivity, no residue after development, good pattern integrity, no or little odor of coating layers after curing, or excellent yellowing resistance.

19 Claims, No Drawings

(51) Int. Cl.

| | | |
|---|---|---|
| C09D 11/101 | (2014.01) | |
| C09D 11/107 | (2014.01) | |
| G03F 7/029 | (2006.01) | |
| C08K 5/17 | (2006.01) | |
| C08K 5/3435 | (2006.01) | |
| C08K 5/357 | (2006.01) | |

(56) References Cited

U.S. PATENT DOCUMENTS

| | | | |
|---|---|---|---|
| 4,666,824 | A | 5/1987 | Messer |
| 4,950,581 | A | 8/1990 | Koike et al. |
| 5,077,402 | A | 12/1991 | Desobry et al. |
| 5,527,925 | A | 6/1996 | Chabrecek et al. |
| 5,612,389 | A | 3/1997 | Chabrecek et al. |
| 5,612,391 | A | 3/1997 | Chabrecek et al. |
| 5,621,018 | A | 4/1997 | Chabrecek et al. |
| 6,087,412 | A | 7/2000 | Chabrecek et al. |
| 6,099,122 | A | 8/2000 | Chabrecek et al. |
| 6,204,306 | B1 | 3/2001 | Chabrecek et al. |
| 6,492,514 | B1 | 12/2002 | Meneguzzo et al. |
| 9,316,906 | B2 | 4/2016 | Shin et al. |
| 9,684,238 | B2 | 6/2017 | Harihara et al. |
| 9,873,663 | B2 | 1/2018 | Oh et al. |
| 2005/0266341 | A1 | 12/2005 | Kim |
| 2015/0111152 | A1 | 4/2015 | Shin et al. |
| 2015/0259321 | A1 | 9/2015 | Harihara et al. |
| 2016/0046551 | A1 | 2/2016 | Shiota et al. |
| 2017/0160636 | A1 | 6/2017 | Tadokoro et al. |
| 2018/0050973 | A1 | 2/2018 | Shiota et al. |
| 2019/0155153 | A1 | 5/2019 | Qian |
| 2020/0264508 | A1* | 8/2020 | Qian .................. G03F 7/039 |

FOREIGN PATENT DOCUMENTS

| | | | |
|---|---|---|---|
| CN | 104661997 A | 5/2015 | |
| CN | 104684888 A | 6/2015 | |
| CN | 104892512 A | 9/2015 | |
| CN | 105916837 A | 8/2016 | |
| CN | 106883114 A | 6/2017 | |
| EP | 2913323 | 9/2015 | |
| EP | 3165965 | 5/2017 | |
| EP | 3392232 | 10/2018 | |
| GB | 1189514 | 3/2002 | |
| JP | 2001-348412 A | 12/2001 | |
| JP | 2009-019142 * | 1/2009 | |
| JP | 2009019142 | 1/2009 | |
| JP | 2009-029859 A | 2/2009 | |
| JP | 2010024291 | 2/2010 | |
| JP | 2017533288 | 11/2017 | |
| JP | 2019528331 | 10/2019 | |
| JP | 6725663 | 6/2020 | |
| KR | 10-2014-0076607 | 6/2014 | |
| KR | 10-2014-0144809 A | 12/2014 | |
| KR | 1020140144809 * | 12/2014 | |
| KR | 10-2015-0040372 | 4/2015 | |
| KR | 101567837 | 11/2015 | |
| KR | 10-2017-0032372 | 3/2017 | |
| WO | 2005014515 | 2/2005 | |
| WO | 2013165207 | 11/2013 | |
| WO | 2014050738 | 4/2014 | |
| WO | 2015108386 | 7/2015 | |
| WO | 2015084114 | 11/2015 | |
| WO | 2016010036 | 1/2016 | |
| WO | 2016078603 | 5/2016 | |
| WO | WO 2017/101553 A1 | 6/2017 | |
| WO | WO-2017101553 A1 * | 6/2017 | ........... C07D 273/01 |
| WO | WO 2018/049976 A1 | 3/2018 | |

OTHER PUBLICATIONS

Cheng et al, WO 2017101553 Machine Translation, Jun. 22, 2017 (Year: 2017).*
Morishi et al, JP 2009-019142 Machine Translation, Jan. 29, 2009 (Year: 2009).*

International Search Report as issued in International Patent Application No. PCT/CN2018/076209, dated May 10, 2018.
Written Opinion of the International Searching Authority as issued in International Patent Application No. PCT/CN2018/076209, dated May 10, 2018.
Database Registry[online]. STN International, Columbus, Ohio, USA, Oct. 27, 2016 (Oct. 27, 2016), CAS RN 2020359-04-8.
Japanese Office Action issued in corresponding Japanese Patent Application No. 2019-544745, dated Aug. 6, 2020.
Extended European Search Report issued in corresponding European Patent Application No. 18755112.2, dated Nov. 23, 2020.
Robertson, David W. et al.: "Structure-Acitivity Relationships of (Arylalkyl)imidazole Anticonvuisants: Comparison of the (Fluorenylalkyl)imidazoles with Nafimldone and Denzimol", J. Med. Chem., 29, 9, 1577-1586 (1986).
Bachmann, et al., "The Rates of Dissociation of Pentaarylethanes", Contribution from the Chemistry Laboratory of the University of Michigan, Journal of Organic Chemistry, vol. 8, pp. 320-330 (1943).
Bolton et al., "The Stability of Carbonium Ions", Journal of the Chemical Society, pp. 1464-1466 (1964).
Chardonnens, et al., "Fluorenacenes and Fluorenaphenes, Synthesis of a Series of Indenofluorenes XVII. Methyl Derivatives of cis-Fluorenacene, trans-Fluorenacene and trans-Fluorenaphene", Helvetica Chimica Acta. vol. 57 (3), pp. 585-599 (1974).
Extended European Search Report dated Apr. 1, 2020, issued in corresponding European App. No. 17850178.9.
Horhold, et al., "Synthesis and Photoconductivity of Poly (2,7-fluorenylene-1,2-diphenylvinylen)", Studies on Poly(arylenevinylenes), Acta Polymerica, vol. 37(6), pp. 369-375 (1986).
International Search Report and Written Opinion dated Nov. 16, 2017, issued in corresponding PCT App. No. PCT/CN2017/099294.
Minabe et al., "Synthese and Some Properties of 9,2': 7', 9', 9"- , and 9,4': 9', 9"- Terfluorene", Bulletin of the Chemical Society of Japan, vol. 51:11, pp. 3373-3376.
Office Action dated Aug. 22, 2019 issued inn connection with Chinese App. No. 201710530354.0.
Office Action dated Jan. 28, 2020 issued in connection with Japanese App. No. 2019-501481.
Office Action dated Mar. 27, 2020 issued in connection with Chinese App. No. 201610821992.3.
Park, et al., "Design annd Sythesis of New Fluorene-Based Blue Light Emitting Polymer Containing Electron Donating Alkoxy Groups and Electron Withdrawing Oxadiazole", Macromolecular Research, vol. 15(3), pp. 216-220 (2007).
PubChem Bethesda (MD): National Library of Medicine (US), National Center for Biotechnology Information; 2004-. PubChem Compound Summary for CID 97070, Methanone, 9H-fluoren-2-ylphenyl-. Available from: pubchem.ncbi.nlm.nih.gov/compound/Methanone_-9H-fluoren-2-yl (cited in an Office Action dated Oct. 14, 2020).
Xuong, et al., "Potential Chemical Pituitary Inhibitors of the Polyarylethylene Series", Department of Organic Chemistry, Radium Institute, University of Paris, Journal of the Chemical Society, pp. 3741-3744 (1952).
Morand, et al., "The Effect of Substituted Carboxylic Acids on Hepatic Cholesterogensis", Journal of Medicinal Chemistry, U.S. American Chemical Society, vol. 7, No. 7, pp. 504-508 (1964).
International Search Report dated Dec. 30, 2016, issued in International App. No. PCT/CN2016/100601, with English translation.
Written Opinion dated Dec. 30, 2016, issued in International App. No. PCT/CN2016/100601, with English translation.
Office Action dated May 8, 2019, issued in JP App. No. 2018-530699, with English translation.
Office Action dated Mar. 1, 2019, issued in JP App. No. 2018-517-895, with English translation.
Office Action dated Jul. 4, 2019, issued in JP App. No. 2018-517895, with English translation.
Office Action dated Feb. 28, 2019, issued in CN App. No. 201510937328.0, with English translation.
Office Action dated Jun. 4, 2019, issued in CN App. No. 201610210118.6, with English translation.
Notice of Allowance dated Oct. 9, 2019, issued in CN App. No. 201510937328.0, with English translation.

(56) References Cited

OTHER PUBLICATIONS

Extended Search Report dated Jul. 29, 2019, issued in EP App. No. 16874613.9.
Office Action dated Nov. 21, 2019, issued in Korean App. No. 10-2018-7019720, with English translation.
Office Action dated Feb. 3, 2020, issued in Chinese App. No. 201610210118.6, with English translation.
Office Action dated Nov. 29, 2019, issued in Korean App. No. 10-2018-7012617, with English translation.
Notice of Allowance dated Feb. 3, 2020, issued in Korean App. No. 10-2018-7019720, with English translation.
Office Action dated May 27, 2020, issued in KR App. No. 10-2018-7012617.
U.S. Restriction Requirement issued in corresponding U.S. Appl. No. 16/061,490, dated Nov. 18, 2020.
U.S. Office Action issued in corresponding U.S. Appl. No. 16/061,490, dated Feb. 12, 2021.

* cited by examiner

FLUORENYLAMINOKETONE PHOTOINITIATOR, PREPARATION METHOD THEREOF, AND UV PHOTOCURABLE COMPOSITION CONTAINING SAME

This application is the U.S. national phase entry of PCT patent application no. PCT/CN2018/076209, which was filed on Feb. 11, 2018, which claims the benefit of priority of Chinese Patent Application No. 201710353951.0, which was filed on May 18, 2017, and Chinese Patent Application No. 201710088234.X, which was filed on Feb. 17, 2017.

TECHNICAL FIELD

The present invention relates to the technical field of novel UV-light radiation radical polymerizable material, and particularly to a fluorenylaminoketone photoinitiator, a preparation method thereof, and a UV photocurable composition containing same.

BACKGROUND ART

Alpha-aminoalkylphenone photoinitiators are a kind of photoinitiator having very high reactivity. Here, commercial photoinitiators include 2-benzyl-2-dimethylamino-1-(4-morpholinophenyl)butanone and 2-(4-methylbenzyl)-2-dimethylamino-1-(4-morpholinophenyl)butanone, which are alpha-aminoalkylphenone photoinitiators produced by Ciba Co., Ltd., under trade names of "Irgacure 369" and "Irgacure 379", respectively, which structures are as follows:

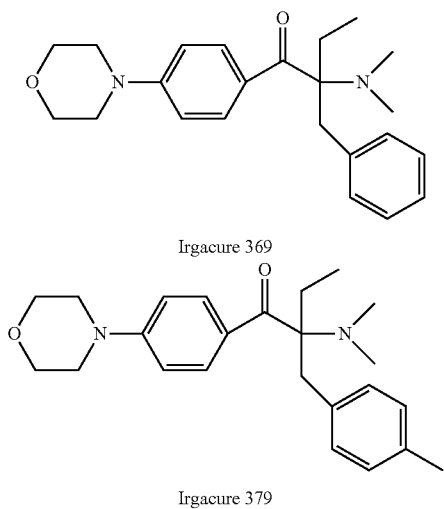

This kind of photoinitiator is usually used in combination with thioxanthone photoinitiators in photocuring of colored systems, and exhibit excellent photoinitiator properties. For example, this kind of photoinitiator is widely used in ceramic inkjet technology. However, these photoinitiators are poorly compatible with matrix resins, and a large amount of organic solvent is often needed to be added, which is disadvantageous to the health of the production operator and results in certain environmental pollution also. Furthermore, with the addition of solvent, ink will easily diffuse and patterns become unclear, and decorative effects of high resolution and high precision cannot be achieved. On the other hand, due to use in colored systems, there are disadvantages of low curing speed, difficulty in complete curing of deep parts, and limited thickness of coating layers in terms of properties, and the applications thereof are thereby limited.

In 2001, patent document JP2001348412A disclosed a liquid curable resin composition using 2-methyl-1-[4-(methylthio)phenyl]-2-(4-morpholinyl)-1-acetone (trade name: Irgacure 907) as a photoinitiator component. However, a methylthio group is contained in an aromatic ring system in the structure of this compound, and there will be inevitably problems of generation of bad odor after decomposition by light irradiation and serious yellowing of cured products. This cannot be used in the fields of food packages, varnish coatings, white ink, and the like.

With respect to the deficiencies described above, there are related reports about research on substitutes for Irgacure 907 photoinitiator in recent years. For example, patent application no. CN101724099 discloses a series of alpha-aminoketone compounds as biphenyl derivatives, wherein 1-([1,1-biphenyl]-4-yl)-2-methyl-2-morpholinylpropan-1-one is an effective substitute for Irgacure 907. This compound does not contain a sulfur element, and exhibits excellent yellowing resistance and will not generate any bad odor after decomposition by light irradiation when used in a UV radical photopolymerizable curing system. However, it is found in practical applications that this photoinitiator has poor solubility and will easily sublimate, leading to pollution of production facilities and light sources, and thus it is not a perfect substitute.

These problems have attracted considerable attention in the industry, and applications of UV coatings and UV inks in various fields such as furniture, appliances, automobile interiors, cigarettes, foods, medicines, cosmetics, and the like are greatly limited due to problems of odor, yellowing, toxicity, and the like of photoinitiators. It is currently an important topic in the field of this industry to develop a photocurable composition, which can effectively solve the problems described above and is advantageous in terms of economy and environmental friendliness.

SUMMARY OF THE INVENTION

The present invention aims to provide a fluorenylaminoketone photoinitiator, a preparation method thereof, and a UV photocurable composition containing same, so as to improve the solubility of traditional photoinitiators and reduce the use of micromolecular active diluents.

In order to achieve the object described above, according to an aspect of the present invention, there is provided a fluorenylaminoketone photoinitiator. The photoinitiator comprises a compound having a structure represented by general formula (I) or a derivative compound thereof,

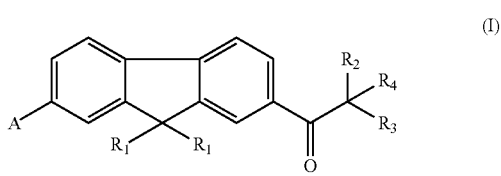

wherein,

A represents hydrogen, a halogen, a nitro group, a $C_1$-$C_{20}$ linear or branched alkyl group, a $C_3$-$C_{10}$ alkylcycloalkyl group, a $C_4$-$C_{10}$ alkylcycloalkyl or cycloalkylalkyl group,

—$COR_6$, or a —CO—$CR_2R_3R_4$ group, wherein, optionally, —$CH_2$— is substituted with O, N, S, or C(=O);

$R_1$ represents hydrogen, a halogen, a $C_1$-$C_{20}$ linear or branched alkyl group, a $C_4$-$C_{20}$ cycloalkylalkyl group, or a $C_2$-$C_{20}$ alkenyl group, wherein, optionally, —$CH_2$— in $R_1$ is substituted with O, N, S, or C(=O), and a ring may be formed between $R_1$s;

$R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in $R_2$ and $R_3$ is substituted with O, N, S, or C(=O), and $R_2$ and $R_3$ may be linked to each other to form a ring;

or $R_2$ represents a $C_1$-$C_{20}$ linear or branched alkyl group or a $C_2$-$C_{20}$ alkenyl group, and $R_3$ is selected from any one of following groups:

a) a group having a chemical formula as follows:

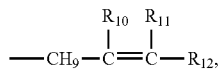

wherein m is 0 or 1, $R_9$ represents hydrogen, a $C_1$-$C_8$ alkyl group, or a phenyl group, and $R_{10}$, $R_{11}$, and $R_{12}$ each independently represent hydrogen or a $C_1$-$C_4$ alkyl group; or b) a group having a chemical formula as follows:

wherein n is 0, 1, 2, or 3; or c) a group having a chemical formula as follows:

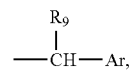

wherein Ar is a substituted or unsubstituted phenyl, naphthyl, furanyl, thienyl, or pyridinyl group;

$R_4$ represents a N-morpholinyl group, a N-piperidinyl group, a N-pyrrolyl group, or a N-dialkyl group, wherein one or more hydrogen atoms in these groups may be substituted with a halogen or a hydroxy group;

$R_5$ and $R_5'$ each independently represent a $C_1$-$C_{20}$ linear or branched alkyl group, a $C_4$-$C_{20}$ cycloalkyl group, a $C_2$-$C_{20}$ alkenyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in these groups may be substituted with —O—; or $R_5$ and $R_5'$ may form a five-membered or six-membered ring by being linked to each other or via —O—, —S—, or —NH—;

$R_6$ represents a $C_1$-$C_{20}$ linear or branched alkyl group, a $C_4$-$C_{20}$ cycloalkyl group, a $C_4$-$C_{20}$ alkylcycloalkyl group, a $C_2$-$C_{20}$ alkenyl group, a $C_6$-$C_{20}$ aryl group, or a $C_6$-$C_{20}$ alkylaryl group, wherein —$CH_2$— in these groups may be substituted with —O— or —S—, and one or more hydrogen atoms in these groups may be independently substituted with a group selected from an alkyl group, a halogen, a nitro group, a cyano group, $SR_7$, and $OR_8$;

$R_7$ and $R_8$ each independently represent hydrogen or a $C_1$-$C_{20}$ linear or branched alkyl group.

Furthermore, the derivative compound of the photoinitiator having a structure represented by general formula (I) comprises derivative compounds obtained by maintaining a main structure of a compound of formula (I) unchanged while allowing branch chain(s) thereof to be substituted or linked to each other.

Furthermore, the derivative compound is a compound having a structure represented by general formula (II) or (III):

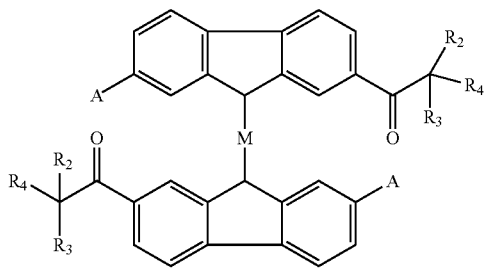

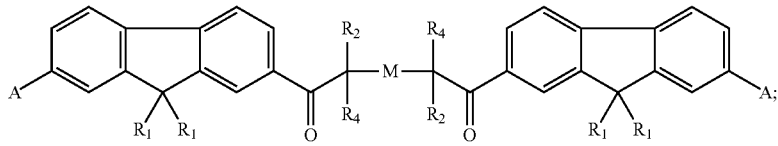

wherein M represents a linking group formed by dimerization and may be absent, a $C_1$-$C_{10}$ linear or branched alkylene group, or a $C_6$-$C_{12}$ arylene or heteroarylene group, and optionally, —$CH_2$— in M is substituted with sulfur, oxygen, NH, or a carbonyl group, and optionally, a hydrogen atom is substituted with OH or $NO_2$.

According to another aspect of the present invention, there is provided a UV photocurable composition containing a fluorenylaminoketone photoinitiator. The UV photocurable composition comprises: an olefinically unsaturated photopolymerizable compound and a photoinitiator; wherein the photoinitiator is the fluorenylaminoketone photoinitiator of any one described above.

Furthermore, the photoinitiator comprising a photoinitiator having a structure represented by general formula (I) or the derivative compound thereof is a mixture of two or more of the compounds.

Furthermore, the olefinically unsaturated photopolymerizable compound is a compound comprising one carbon-carbon double bond, and preferably an acrylate compound or a methacrylate compound; or the olefinically unsaturated photopolymerizable compound is a compound comprising two or more carbon-carbon double bonds, and preferably an acrylate or methacrylate of an alkylene glycol or polyol, an acrylate of a polyester polyol, a polyether polyol, an epoxy polyol, or a polyurethane polyol, a vinyl ether, and an unsaturated polyester of an unsaturated dicarboxylic acid and a polyol.

Furthermore, when the UV photocurable composition is used as a UV etching resist ink or a UV solder resist ink, at least one compound of the olefinically unsaturated photopolymerizable compounds used contains an alkali-soluble group, preferably a carboxyl-containing resin.

Furthermore, the carboxyl-containing resin is a (meth)acrylate, an ethylenically unsaturated carboxylic acid, or a (meth)acrylate-based polymer; preferably, the (meth)acrylate is one or more selected from the group consisting of methyl (meth)acrylate, ethyl (meth)acrylate, butyl (meth)acrylate, cyclohexyl (meth)acrylate, benzyl (meth)acrylate, diethylaminoethyl (meth)acrylate, dimethylaminoethyl (meth)acrylate, hydroxyethyl (meth)acrylate, hydroxypropyl (meth)acrylate, furfuryl (meth)acrylate, and glycidyl (meth)acrylate; preferably, the ethylenically unsaturated carboxylic acid is one or more selected from the group consisting of acrylic acid, methacrylic acid, vinylbenzoic acid, maleic acid, alkyl maleate, fumaric acid, itaconic acid, butenic acid, cinnamic acid, an acrylic acid dimer, an addition product of a monomer having a hydroxy group and a cyclic acid anhydride, and an ω-carboxyl-polycaprolactone-(meth)acrylate, and more preferably (meth)acrylic acid; preferably, the (meth)acrylate-based polymer is one or more selected from the group consisting of (meth)acrylamide, n-butyl (meth)acrylate, styrene, vinylnaphthalene, (meth)acrylonitrile, vinyl acetate, and vinylcyclohexane.

Furthermore, the UV photocurable composition further comprises another photoinitiator, and preferably, the another photoinitiator is one or more selected from the group consisting of benzophenone, benzildimethyl ketal, 2-hydroxy-2-methyl-1-phenyl-acetone, 1-hydroxy-cyclohexyl-phenyl-one, isopropylthioxanthene, (2,4,6-trimethyl-benzoyl) diphenylphosphine oxide, and bis(2,4,6-trimethyl benzoyl)-phenylphosphine oxide.

Furthermore, the UV photocurable composition further comprises a sensitizer; preferably, the sensitizer is a pyrazoline compound, an acridine compound, an anthracene compound, a coumarin compound, or a tertiary amine compound.

Furthermore, the UV photocurable composition further comprises a colorant, which is an inorganic pigment or an organic pigment.

Furthermore, the UV photocurable composition further comprises an additive, which includes one or more of a surfactant, a wetting agent, a dispersant, a rheology modifier, a defoamer, and a storage enhancer.

According to still another aspect of the present invention, there is provided a preparation method of the fluorenylaminoketone photoinitiator described above, comprising steps of:

(1) subjecting a raw material a and a raw material b to Friedel-Crafts reaction to generate an intermediate a with a reaction formula as follows:

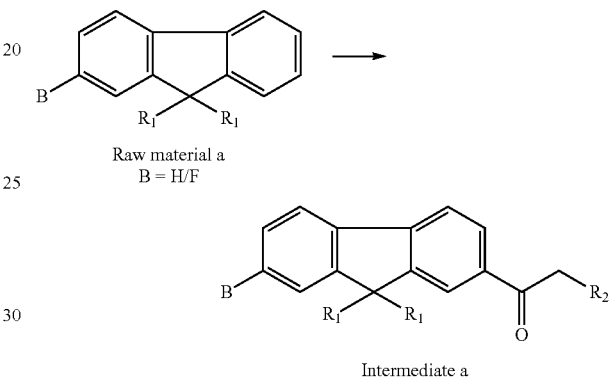

(2) subjecting the intermediate a to substitution reaction to generate an intermediate b:

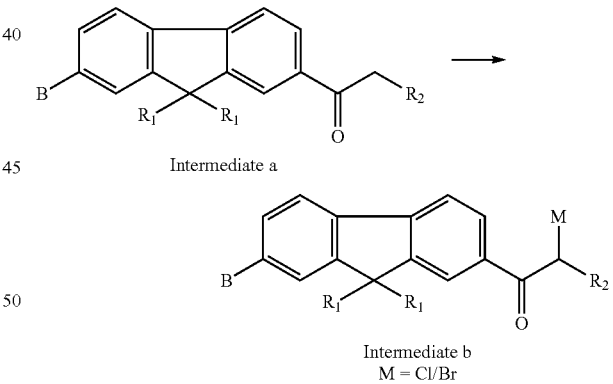

(3) subjecting the intermediate b is to substitution reaction to generate an intermediate c:

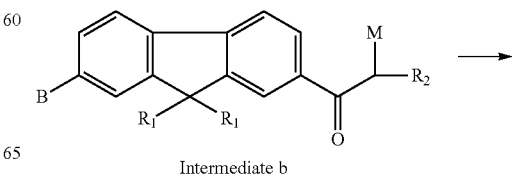

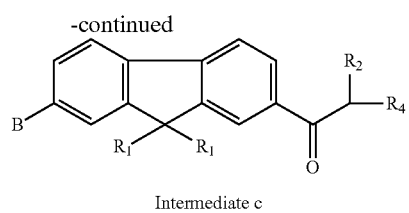

Intermediate c (4) subjecting the intermediate c to Stevens rearrangement reaction to generate an intermediate d:

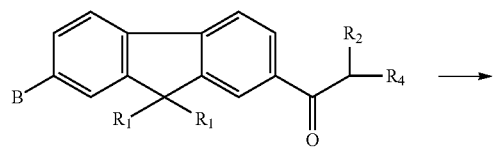

Intermediate c

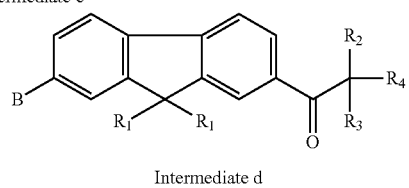

Intermediate d (5) if a product in which A=H is expected to be obtained, then B=H in the raw material a, and the intermediate d is a compound of general formula (I);
if a product in which

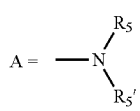

is expected to be obtained, then B=F in the raw material a, subjecting the intermediate d to substitution reaction to generate a compound having general formula (I) as follows;

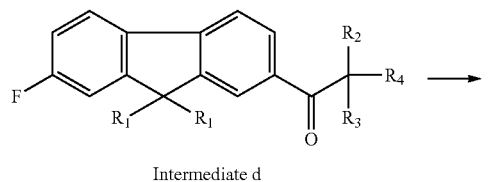

Intermediate d

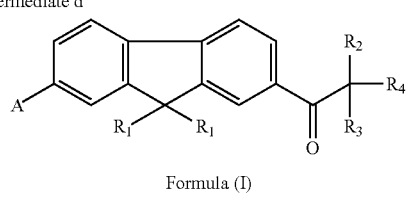

Formula (I)

if a product in which

is expected to be obtained, then B=H in the raw material a, subjecting the intermediate d to Friedel-Crafts reaction to generate a compound having general formula (I) as follows;

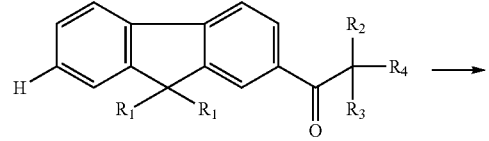

Intermediate d

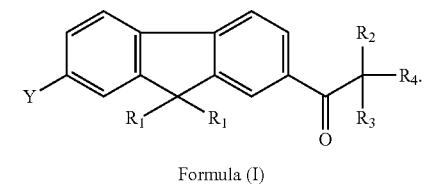

Formula (I)

Furthermore, in step (1), the intermediate a and the raw material are subjected to Friedel-Crafts reaction under a catalytic condition to generate an intermediate b, wherein the raw material b is

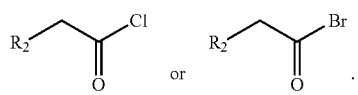

Furthermore, in step (2), the intermediate a and raw material c are subjected to substitution reaction in an organic solvent to generate an intermediate b, wherein the raw material c is thionyl chloride or liquid bromine.

Furthermore, in step (3), the intermediate b and raw material d are subjected to substitution reaction in an organic solvent to generate an intermediate c, wherein the raw material d is HX.

Furthermore, in step (4), the intermediate c and raw material e are subjected to Stevens rearrangement reaction in an organic solvent under a basic condition to generate an intermediate d, wherein the raw material e is $R_3$—Br.

Furthermore, in step (5), if a product in which A=H is expected to be obtained, then B=H in the raw material a, and the intermediate d is a compound of general formula (I); if a product in which

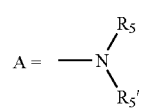

is expected to be obtained, then B=F in the raw material a, and the intermediate d and raw material f are subjected to substitution reaction in an organic solvent under a basic condition to generate a compound represented by general formula (I), wherein the raw material f is HA; if a product in which

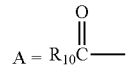

is expected to be obtained, then B=H in the raw material a, and the intermediate d and raw material g are subjected to Friedel-Crafts reaction under a catalytic condition to generate a compound represented by general formula (I), wherein the raw material g is ACl or ABr.

According to yet another aspect of the present invention, there is provided use of the UV photocurable composition described above in UV coatings and UV inks.

In order to achieve the object described above, according to an aspect of the present invention, there is provided a UV photocurable composition containing a fluorenylaminoketone photoinitiator. The UV photocurable composition comprises: an olefinically unsaturated photopolymerizable compound and a photoinitiator; wherein the photoinitiator comprises a compound having a structure represented by general formula (I) or a derivative compound thereof,

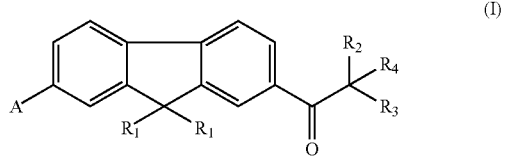

(I)

wherein,

A represents hydrogen, a halogen, a nitro group, a $C_1$-$C_{20}$ linear or branched alkyl group, a $C_3$-$C_{10}$ alkylcycloalkyl group, a $C_4$-$C_{10}$ alkylcycloalkyl or cycloalkylalkyl group,

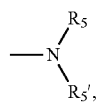

—$COR_6$, or a —CO—$CR_2R_3R_4$ group, wherein, optionally, —$CH_2$— is substituted with O, N, S, or C(=O);

$R_1$ represents hydrogen, a halogen, a $C_1$-$C_{20}$ linear or branched alkyl group, a $C_4$-$C_{20}$ cycloalkylalkyl group, or a $C_2$-$C_{20}$ alkenyl group, wherein, optionally, —$CH_2$— in $R_1$ is substituted with O, N, S, or C(=O), and a ring may be formed between $R_1$s;

$R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in $R_2$ and $R_3$ is substituted with O, N, S, or C(=O), and $R_2$ and $R_3$ may be linked to each other to form a ring;

$R_4$ represents a N-morpholinyl group, a N-piperidinyl group, a N-pyrrolyl group, or a N-dialkyl group, wherein one or more hydrogen atoms in these groups may be substituted with a halogen or a hydroxy group;

$R_5$ and $R_5'$ each independently represent a $C_1$-$C_{20}$ linear or branched alkyl group, a $C_4$-$C_{20}$ cycloalkyl group, a $C_2$-$C_{20}$ alkenyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in these groups may be substituted with —O—; or $R_5$ and $R_5'$ may form a five-membered or six-membered ring by being linked to each other or via —O—, —S—, or —NH—;

$R_6$ represents a phenyl group which is unsubstituted or substituted with one or more of a $C_1$-$C_{20}$ alkyl group, a halogen, a cyano group, $SR_7$, and $OR_8$;

$R_7$ and $R_8$ each independently represent hydrogen or a $C_1$-$C_{20}$ linear or branched alkyl group.

Furthermore, the usage amount of the olefinically unsaturated photopolymerizable compound is 5-95 parts by mass, and the usage amount of the photoinitiator is 0.05-15 parts by mass.

Furthermore, the usage amount of the olefinically unsaturated photopolymerizable compound is 10-90 parts by mass, and the usage amount of the photoinitiator is 1-10 parts by mass.

Furthermore, the photoinitiator having a structure represented by general formula (I) is one or more selected from the group consisting of

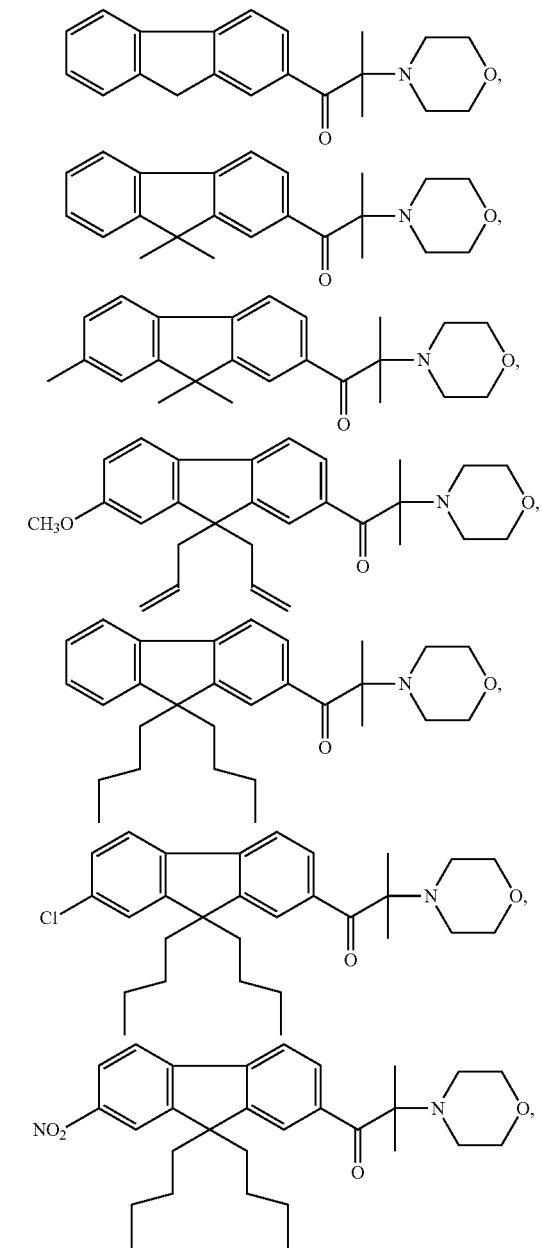

11
-continued
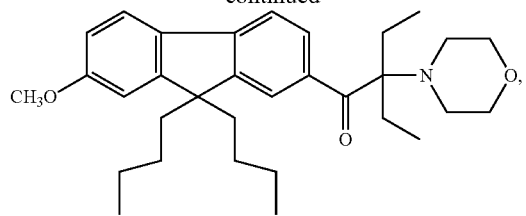
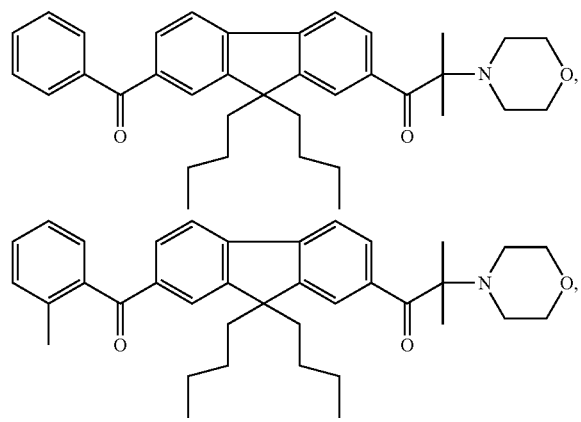
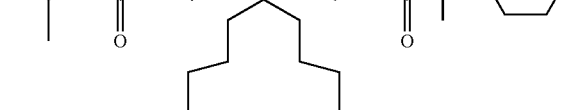
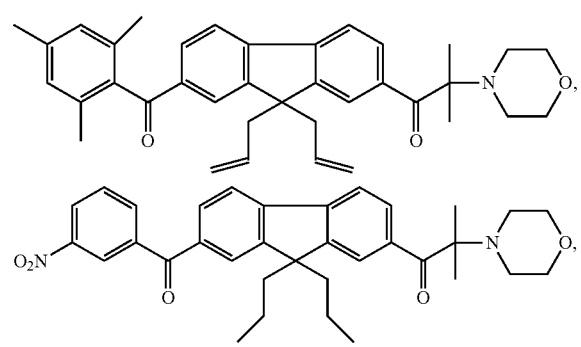
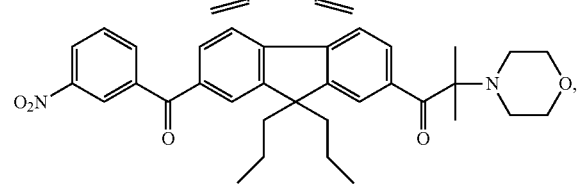
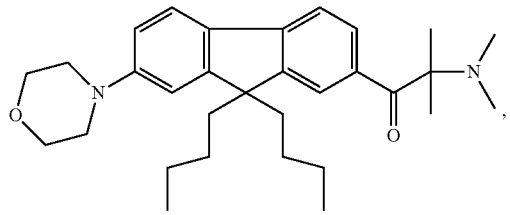
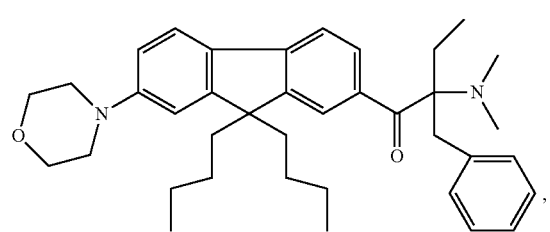
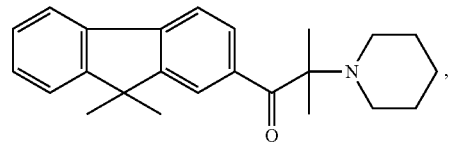
12
-continued
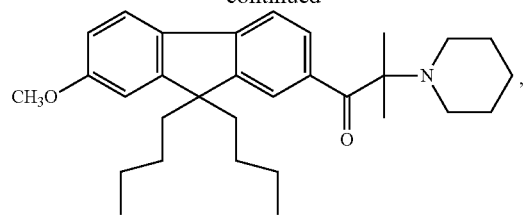
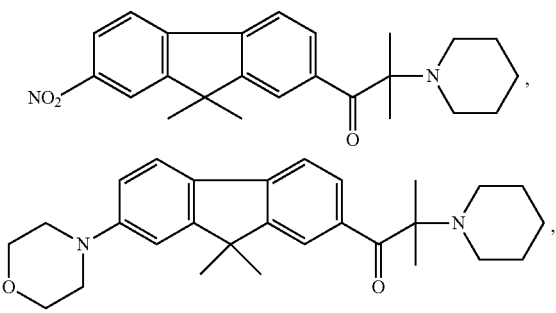
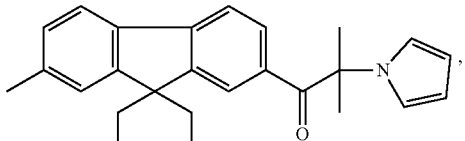
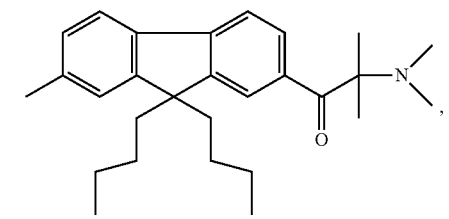
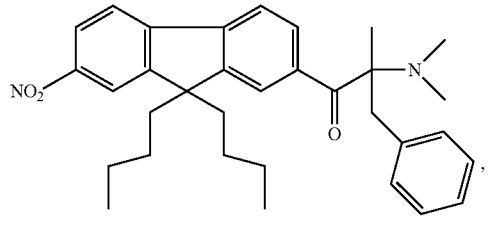
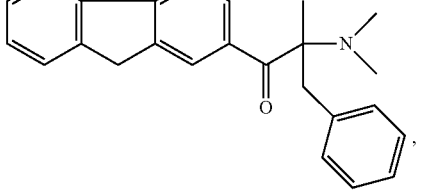
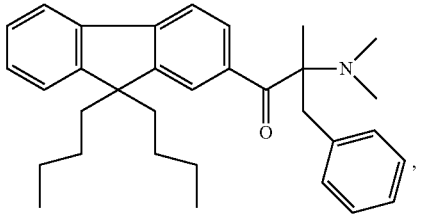

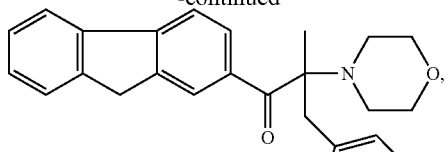

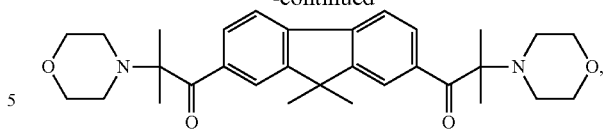

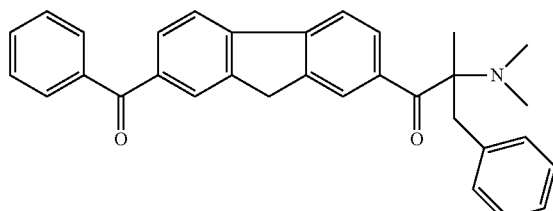

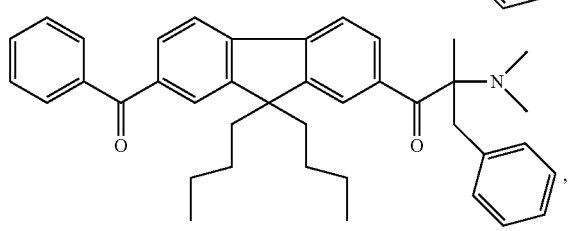

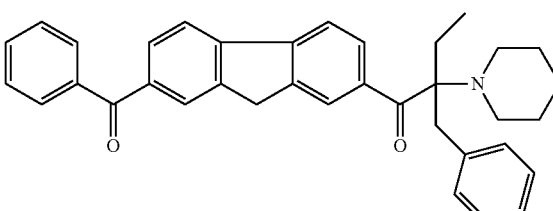

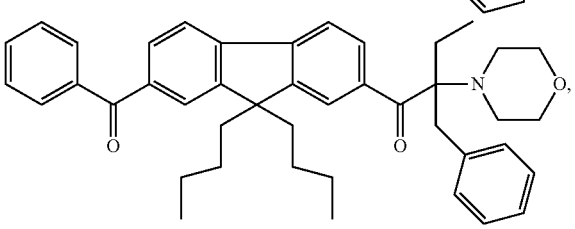

Furthermore, the derivative compound of the photoinitiator having a structure represented by general formula (I) comprises derivative compounds obtained by maintaining a main structure of a compound of formula (I) unchanged while allowing branch chain(s) thereof to be substituted or linked to each other.

Furthermore, the derivative compound is a compound having a structure represented by general formula (II) or (III):

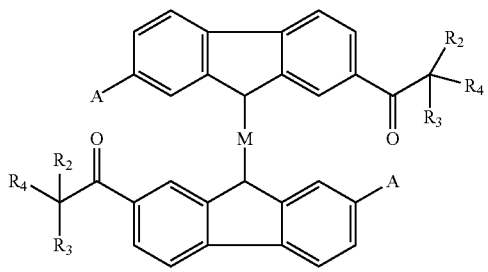

(II)

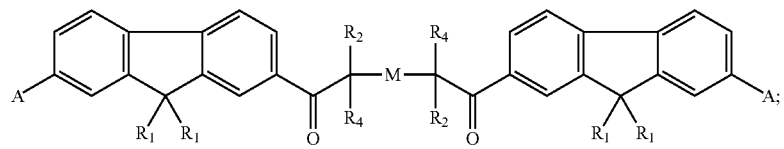

(III)

wherein M represents a linking group formed by dimerization and may be absent, a $C_1$-$C_{10}$ linear or branched alkylene group, or a $C_6$-$C_{12}$ arylene or heteroarylene group, and optionally, —$CH_2$— in M is substituted with sulfur, oxygen, NH, or a carbonyl group, and optionally, a hydrogen atom is substituted with OH or $NO_2$.

Furthermore, the derivative compound is

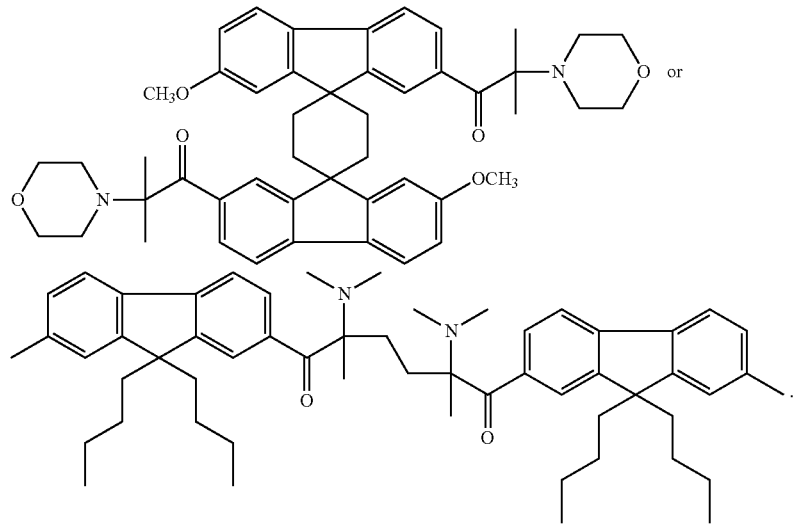

Furthermore, the photoinitiator comprising a photoinitiator having a structure represented by general formula (I) or the derivative compound thereof is a mixture of two or more of the compounds.

Furthermore, the olefinically unsaturated photopolymerizable compound is a monomer compound or an oligomer.

Furthermore, the olefinically unsaturated photopolymerizable compound is a compound comprising one carbon-carbon double bond, and preferably an acrylate compound or a methacrylate compound; or the olefinically unsaturated photopolymerizable compound is a compound comprising two or more carbon-carbon double bonds, and preferably an acrylate or methacrylate of an alkylene glycol or polyol, an acrylate of a polyester polyol, a polyether polyol, an epoxy polyol, or a polyurethane polyol, a vinyl ether, and an unsaturated polyester of an unsaturated dicarboxylic acid and a polyol.

Furthermore, when the UV photocurable composition is used as a UV etching resist ink or a UV solder resist ink, at least one compound of the olefinically unsaturated photopolymerizable compounds used contains an alkali-soluble group, preferably a carboxyl-containing resin.

Furthermore, the carboxyl-containing resin is a (meth)acrylate, an ethylenically unsaturated carboxylic acid, or a (meth)acrylate-based polymer;

preferably, the (meth)acrylate is one or more selected from the group consisting of methyl (meth)acrylate, ethyl (meth)acrylate, butyl (meth)acrylate, cyclohexyl (meth)acrylate, benzyl (meth)acrylate, diethylaminoethyl (meth)acrylate, dimethylaminoethyl (meth)acrylate, hydroxyethyl (meth)acrylate, hydroxypropyl (meth)acrylate, furfuryl (meth)acrylate, and glycidyl (meth)acrylate;

preferably, the ethylenically unsaturated carboxylic acid is one or more selected from the group consisting of acrylic acid, methacrylic acid, vinylbenzoic acid, maleic acid, alkyl maleate, fumaric acid, itaconic acid, butenic acid, cinnamic acid, an acrylic acid dimer, an addition product of a monomer having a hydroxy group and a cyclic acid anhydride, and an ω-carboxyl-polycaprolactone-(meth)acrylate, and more preferably (meth)acrylic acid;

preferably, the (meth)acrylate-based polymer is one or more selected from the group consisting of (meth)acrylamide, n-butyl (meth)acrylate, styrene, vinylnaphthalene, (meth)acrylonitrile, vinyl acetate, and vinylcyclohexane.

Furthermore, the UV photocurable composition further comprises another photoinitiator, and preferably, the another photoinitiator is one or more selected from the group consisting of benzophenone, benzildimethyl ketal, 2-hydroxy-2-methyl-1-phenyl-acetone, 1-hydroxy-cyclohexyl-phenyl-one, isopropylthioxanthene, (2,4,6-trimethyl-benzoyl)diphenylphosphine oxide, and bis(2,4,6-trimethyl benzoyl)-phenylphosphine oxide.

Furthermore, the UV photocurable composition further comprises a sensitizer; preferably, the sensitizer is a pyrazoline compound, an acridine compound, an anthracene compound, a coumarin compound, or a tertiary amine compound. More preferably, the usage amount of the sensitizer is 0-5 parts by mass, and further preferably, the usage amount of the sensitizer is 0-2 parts by mass.

Furthermore, the UV photocurable composition further comprises a colorant, which is an inorganic pigment or an organic pigment. The usage amount of the colorant is 0-50 parts by mass, and preferably, the usage amount of the colorant is 0-20 parts by mass.

Furthermore, the UV photocurable composition further comprises an additive, which includes one or more of a surfactant, a wetting agent, a dispersant, a rheology modifier, a defoamer, and a storage enhancer. Preferably, the usage amount of the additive is 0-5 parts by mass, and more preferably, the usage amount of the additive is 0-3 parts by mass.

According to another aspect of the present invention, there is provided use of any one of the UV photocurable compositions described above in UV coatings and UV inks.

Furthermore, the UV inks include a UV etching resist ink, a UV solder resist ink, a flexographic printing ink, an offset printing ink, and the like.

The fluorenylaminoketone photoinitiator provided by the present invention can effectively improve the solubility of traditional photoinitiators and reduce the use of micromolecular active diluents, and also has high sensitivity and good effect of deep curing. It has very good promotion effect on popularization and application of photocurable compositions, particularly colored ink systems, in the field of photocuring.

Additionally, all of the raw materials used in the preparation method of the present invention are compounds which are known in the prior art, commercially available, or conveniently prepared by known synthetic methods. The preparation method is simple and has a high product purity, and is very suitable for industrial production.

The UV photocurable composition of the present invention containing a fluorenylaminoketone photoinitiator has advantages of high sensitivity, no residue after development, good pattern integrity, and no or little odor of coating layers after curing, as well as excellent yellowing resistance.

DESCRIPTION OF EMBODIMENTS

It is to be indicated that Examples in this application and features in the Examples may be combined with each other where there is no conflict. This invention will be illustrated in detail in conjunction with Examples below.

With respect to deficiencies in the prior art, the present invention has proposed the following technical solutions.

According to a typical embodiment of the present invention, there is provided a fluorenylaminoketone photoinitiator. The photoinitiator comprises a compound having a structure represented by general formula (I) or a derivative compound thereof,

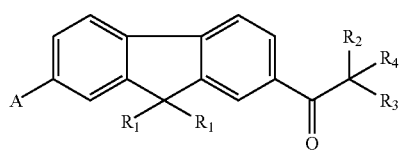

(I)

wherein,

A represents hydrogen, a halogen, a nitro group, a $C_1$-$C_{20}$ linear or branched alkyl group, a $C_3$-$C_{10}$ alkylcycloalkyl group, a $C_4$-$C_{10}$ alkylcycloalkyl or cycloalkylalkyl group,

—$COR_6$, or a —$CO$—$CR_2R_3R_4$ group, wherein, optionally, —$CH_2$— is substituted with O, N, S, or C(=O);

$R_1$ represents hydrogen, a halogen, a $C_1$-$C_{20}$ linear or branched alkyl group, a $C_4$-$C_{20}$ cycloalkylalkyl group, or a $C_2$-$C_{20}$ alkenyl group, wherein, optionally, —$CH_2$— in $R_1$ is substituted with O, N, S, or C(=O), and a ring may be formed between $R_1$s;

$R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in $R_2$ and $R_3$ is substituted with O, N, S, or C(=O), and $R_2$ and $R_3$ may be linked to each other to form a ring;

or $R_2$ represents a $C_1$-$C_{20}$ linear or branched alkyl group or a $C_2$-$C_{20}$ alkenyl group, and $R_3$ is selected from any one of following groups:

a) a group having a chemical formula as follows:

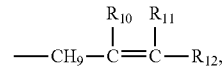

wherein m is 0 or 1, $R_9$ represents hydrogen, a $C_1$-$C_8$ alkyl group, or a phenyl group, and $R_{10}$, $R_{11}$, and $R_{12}$ each independently represent hydrogen or a $C_1$-$C_4$ alkyl group; or b) a group having a chemical formula as follows:

wherein n is 0, 1, 2, or 3; or c) a group having a chemical formula as follows:

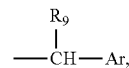

wherein Ar is a substituted or unsubstituted phenyl, naphthyl, furanyl, thienyl, or pyridinyl group;

$R_4$ represents a N-morpholinyl group, a N-piperidinyl group, a N-pyrrolyl group, or a N-dialkyl group, wherein one or more hydrogen atoms in these groups may be substituted with a halogen or a hydroxy group;

$R_5$ and $R_5'$ each independently represent a $C_1$-$C_{20}$ linear or branched alkyl group, a $C_4$-$C_{20}$ cycloalkyl group, a $C_2$-$C_{20}$ alkenyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in these groups may be substituted with —O—; or $R_5$ and $R_5'$ may form a five-membered or six-membered ring by being linked to each other or via —O—, —S—, or —NH—;

$R_6$ represents a $C_1$-$C_{20}$ linear or branched alkyl group, a $C_4$-$C_{20}$ cycloalkyl group, a $C_4$-$C_{20}$ alkylcycloalkyl group, a $C_2$-$C_{20}$ alkenyl group, a $C_6$-$C_{20}$ aryl group, or a $C_6$-$C_{20}$ alkylaryl group, wherein —$CH_2$— in these groups may be substituted with —O— or —S—, and one or more hydrogen atoms in these groups may be independently substituted with a group selected from an alkyl group, a halogen, a nitro group, a cyano group, $SR_7$, and $OR_8$;

$R_7$ and $R_8$ each independently represent hydrogen or a $C_1$-$C_{20}$ linear or branched alkyl group.

The fluorenylaminoketone photoinitiator provided by the present invention can effectively improve the solubility of traditional photoinitiators and reduce the use of micromolecular active diluents, and also has high sensitivity and good effect of deep curing. It has very good promotion effect on popularization and application of photocurable compositions, particularly colored ink systems, in the field of photocuring.

According to a typical embodiment of the present invention, the derivative compound of the photoinitiator having a structure represented by general formula (I) comprises derivative compounds obtained by maintaining a main structure of a compound of formula (I) unchanged while allowing branch chain(s) thereof to be substituted or linked to each other.

Preferably, the derivative compound is a compound having a structure represented by general formula (II) or (III):

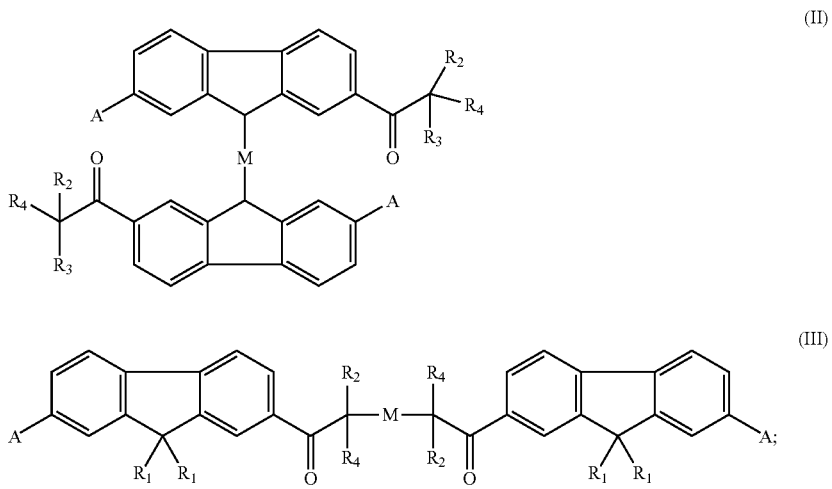

wherein M represents a linking group formed by dimerization and may be absent, a $C_1$-$C_{10}$ linear or branched alkylene group, or a $C_6$-$C_{12}$ arylene or heteroarylene group, and optionally, —$CH_2$— in M is substituted with sulfur, oxygen, NH, or a carbonyl group, and optionally, a hydrogen atom is substituted with OH or $NO_2$.

Exemplarily, the derivative compound described above may be a compound having the following structure:

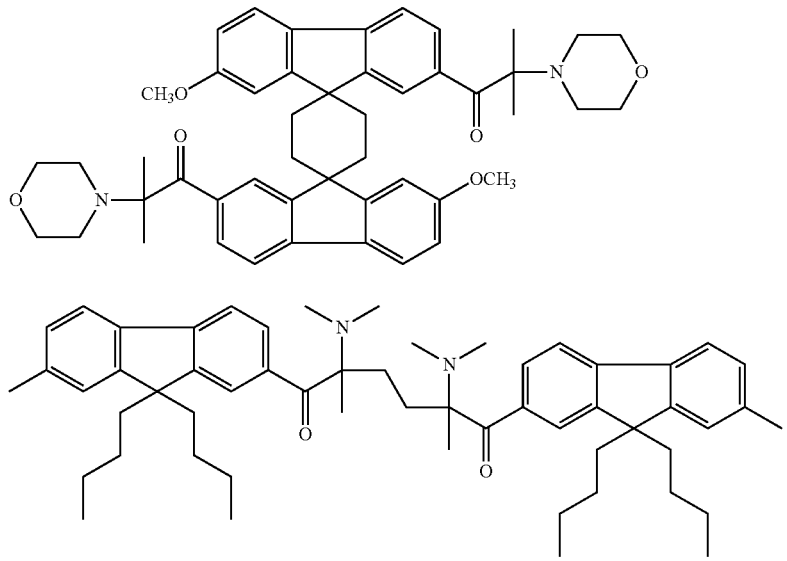

In some cases, it is advantageous to use a mixture of two or more of the initiators described above.

Of course, the photoinitiator having a structure represented by general formula (I) may also be mixed and used with any other known photoinitiator.

According to a typical embodiment of the present invention, there is provided a preparation method of the fluorenylaminoketone photoinitiator described above. The preparation method comprises steps of:

(1) subjecting a raw material a and a raw material b to Friedel-Crafts reaction to generate an intermediate a with a reaction formula as follows:

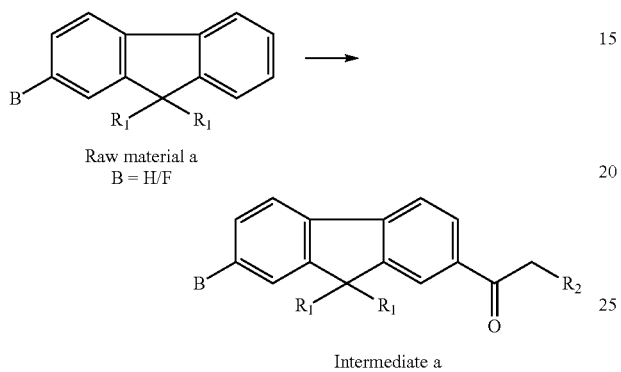

(2) subjecting the intermediate a to substitution reaction to generate an intermediate b:

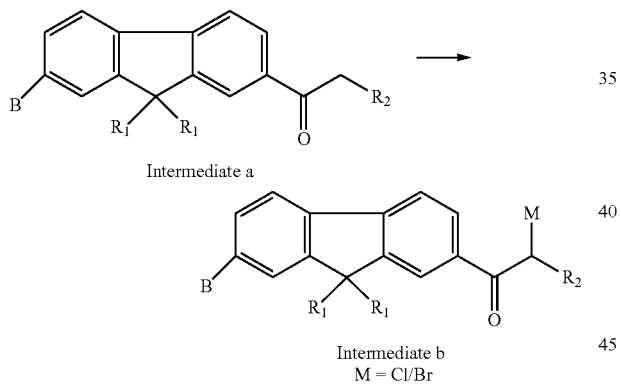

(3) subjecting the intermediate b to substitution reaction to generate an intermediate c:

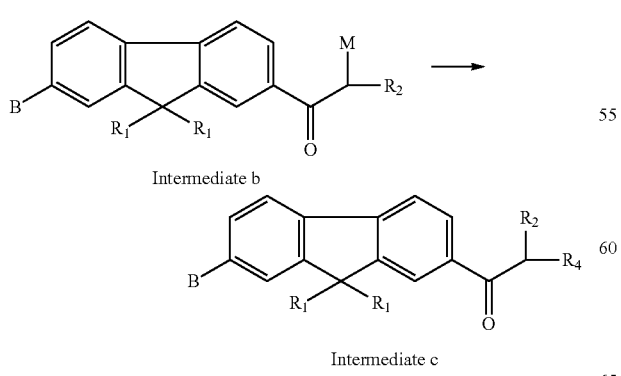

(4) subjecting the intermediate c to Stevens rearrangement reaction to generate an intermediate d:

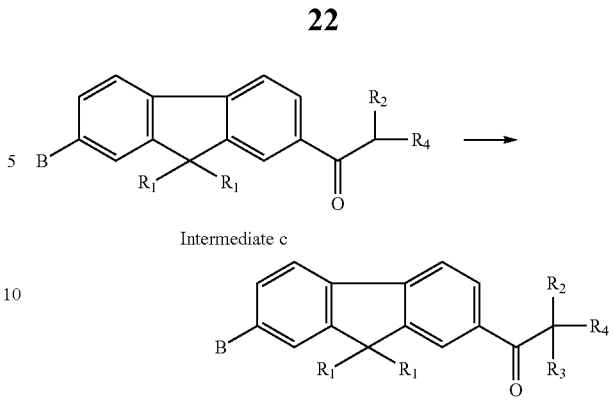

(5) if a product in which A=H is expected to be obtained, then B=H in the raw material a, and the intermediate d is a compound of general formula (I);

if a product in which

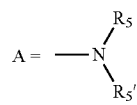

is expected to be obtained, then B=F in the raw material a, subjecting the intermediate d to substitution reaction to generate a compound having general formula (I) as follows;

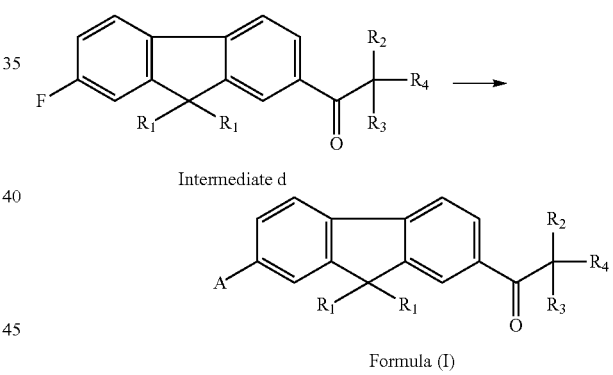

if a product in which

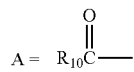

is expected to be obtained, then B=H in the raw material a, subjecting the intermediate d to Friedel-Crafts reaction to generate a compound having general formula (I) as follows;

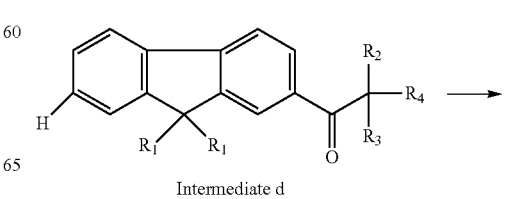

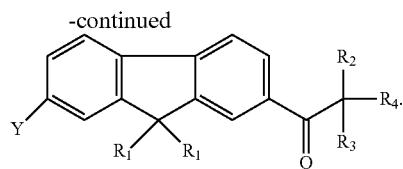

Formula (I)

Preferably, in step (1), the intermediate a and the raw material are subjected to Friedel-Crafts reaction under a catalytic condition to generate an intermediate b, wherein the raw material b is

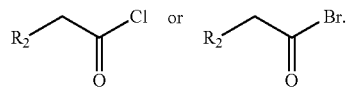

Preferably, in step (2), the intermediate a and raw material c are subjected to substitution reaction in an organic solvent to generate an intermediate b, wherein the raw material c is thionyl chloride or liquid bromine.

Preferably, in step (3), the intermediate b and raw material d are subjected to substitution reaction in an organic solvent to generate an intermediate c, wherein the raw material d is HX.

Preferably, in step (4), the intermediate c and raw material e are subjected to Stevens rearrangement reaction in an organic solvent under a basic condition to generate an intermediate d, wherein the raw material e is $R_3$—Br.

Preferably, in step (5), if a product in which A=H is expected to be obtained, then B=H in the raw material a, and the intermediate d is a compound of general formula (I); if a product in which

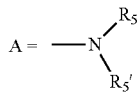

is expected to be obtained, then B=F in the raw material a, and the intermediate d and raw material f are subjected to substitution reaction in an organic solvent under a basic condition to generate a compound represented by general formula (I), wherein the raw material f is HA; if a product in which

is expected to be obtained, then B=H in the raw material a, and the intermediate d and raw material g are subjected to Friedel-Crafts reaction under a catalytic condition to generate a compound represented by general formula (I), wherein the raw material g is ACl or ABr.

All of the raw materials used in the preparation method of the present invention are compounds which are known in the prior art, commercially available, or conveniently prepared by known synthetic methods. Reactions involved in steps (1) to (5) are all traditional reactions for synthesizing similar compounds in the art. On the basis of knowing the idea of synthesis disclosed in the present invention, specific reaction conditions will be easily determined with respect to the person skilled in the art. The preparation method of the present invention is simple and has a high product purity, and is suitable for industrial production.

According to yet another aspect of the present invention, there is provided use of the UV photocurable composition described above in UV coatings and UV inks.

According to a typical embodiment of the present invention, there is provided a UV photocurable composition containing a fluorenylaminoketone photoinitiator. The UV photocurable composition comprises: an olefinically unsaturated photopolymerizable compound and a photoinitiator; wherein the photoinitiator comprises a compound having a structure represented by general formula (I) or a derivative compound thereof,

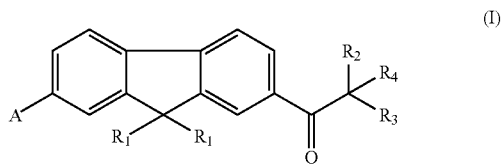

wherein,

A represents hydrogen, a halogen, a nitro group, a $C_1$-$C_{20}$ linear or branched alkyl group, a $C_3$-$C_{10}$ alkylcycloalkyl group, a $C_4$-$C_{10}$ alkylcycloalkyl or cycloalkylalkyl group,

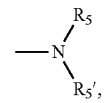

—$COR_6$, or a —CO—$CR_2R_3R_4$ group, wherein, optionally, —$CH_2$— is substituted with O, N, S, or C(=O);

$R_1$ represents hydrogen, a halogen, a $C_1$-$C_{20}$ linear or branched alkyl group, a $C_4$-$C_{20}$ cycloalkylalkyl group, or a $C_2$-$C_{20}$ alkenyl group, wherein, optionally, —$CH_2$— in $R_1$ is substituted with O, N, S, or C(=O), and a ring may be formed between $R_1$s, $R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in $R_2$ and $R_3$ is substituted with O, N, S, or C(=O), and $R_2$ and $R_3$ may be linked to each other to form a ring;

or $R_2$ represents a $C_1$-$C_{20}$ linear or branched alkyl group or a $C_2$-$C_{20}$ alkenyl group, and $R_3$ is selected from any one of following groups:

a) a group having a chemical formula as follows:

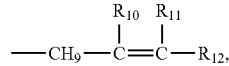

wherein m is 0 or 1, $R_9$ represents hydrogen, a $C_1$-$C_8$ alkyl group, or a phenyl group, and $R_{10}$, $R_{11}$, and $R_{12}$ each independently represent hydrogen or a $C_1$-$C_4$ alkyl group; or b) a group having a chemical formula as follows:

wherein n is 0, 1, 2, or 3; or c) a group having a chemical formula as follows:

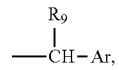

wherein Ar is a substituted or unsubstituted phenyl, naphthyl, furanyl, thienyl, or pyridinyl group;

$R_4$ represents a N-morpholinyl group, a N-piperidinyl group, a N-pyrrolyl group, or a N-dialkyl group, wherein one or more hydrogen atoms in these groups may be substituted with a halogen or a hydroxy group;

$R_5$ and $R_5'$ each independently represent a $C_1$-$C_{20}$ linear or branched alkyl group, a $C_4$-$C_{20}$ cycloalkyl group, a $C_2$-$C_{20}$ alkenyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in these groups may be substituted with —O—; or $R_5$ and $R_5'$ may form a five-membered or six-membered ring by being linked to each other or via —O—, —S—, or —NH—;

$R_6$ represents a $C_1$-$C_{20}$ linear or branched alkyl group, a $C_4$-$C_{20}$ cycloalkyl group, a $C_4$-$C_{20}$ alkylcycloalkyl group, a $C_2$-$C_{20}$ alkenyl group, a $C_6$-$C_{20}$ aryl group, or a $C_6$-$C_{20}$ alkylaryl group, wherein —$CH_2$— in these groups may be substituted with —O— or —S—, and one or more hydrogen atoms in these groups may be independently substituted with a group selected from an alkyl group, a halogen, a nitro group, a cyano group, $SR_7$, and $OR_8$;

$R_7$ and $R_8$ each independently represent hydrogen or a $C_1$-$C_{20}$ linear or branched alkyl group.

The UV photocurable composition of the present invention containing a fluorenylaminoketone photoinitiator has advantages of high sensitivity, no residue after development, good pattern integrity, and no or little odor of coating layers after curing, as well as excellent yellowing resistance.

The preparation process of the UV photocurable composition of the present invention is simple. According to a typical embodiment of the present invention, the components described above may be uniformly stirred and mixed either in a dark room or in a yellow light lamp environment.

According to a typical embodiment of the present invention, the UV photocurable composition further comprises another photoinitiator, and preferably, the another photoinitiator is one or more selected from the group consisting of benzophenone, benzildimethyl ketal, 2-hydroxy-2-methyl-1-phenyl-acetone, 1-hydroxy-cyclohexyl-phenyl-one, isopropylthioxanthene, (2,4,6-trimethyl-benzoyl) diphenylphosphine oxide, and bis(2,4,6-trimethyl benzoyl)-phenylphosphine oxide.

According to a typical embodiment of the present invention, the UV photocurable composition further comprises a colorant, which is an inorganic pigment or an organic pigment. The usage amount of the colorant is 0-50 parts by mass, and preferably, the usage amount of the colorant is 0-20 parts by mass.

According to a typical embodiment of the present invention, the UV photocurable composition further comprises an additive, which includes one or more of a surfactant, a wetting agent, a dispersant, a rheology modifier, a defoamer, and a storage enhancer.

Respective components of the UV photocurable composition of the present invention will be illustrated in more detail below.

1) Olefinically Unsaturated Photopolymerizable Compound

The olefinically unsaturated photopolymerizable compound: a compound having a radical polymerizable olefinically unsaturated bond, which may be a monomer compound (low molecular weight) or an oligomer (relatively high molecular weight).

A compound comprising one carbon-carbon double bond is preferably an acrylate compound or a methacrylate compound, for example, acrylates or methacrylates of monoalcohols such as methyl acrylate, butyl acrylate, 2-ethylhexyl acrylate, cyclohexyl acrylate, isobornyl acrylate, hydroxy-ethyl acrylate, and methyl methacrylate, acrylonitrile, N-dialkylacrylamide, N-vinylpyrrolidone, vinylbenzene, vinyl acetate, and vinyl ether.

A compound comprising two or more carbon-carbon double bonds includes an acrylate or methacrylate of an alkylene glycol or polyol, an acrylate of a polyester polyol, a polyether polyol, an epoxy polyol, or a polyurethane polyol, a vinyl ether, and an unsaturated polyester of an unsaturated dicarboxylic acid and a polyol, for example, polyethylene glycol diacrylate, neopentyl glycol diacrylate, trimethylolpropane triacrylate, multi-ethoxylated trimethylolpropane triacrylate, pentaerythritol tetraacrylate, dipentaerythritol hexaacrylate, a polyester oligomer acrylate, a polyurethane oligomer acrylate, an aromatic epoxy resin acrylate, and polyethylene glycol maleate.

when the UV photocurable composition is used as a UV etching resist ink or a UV solder resist ink, at least one compound of the olefinically unsaturated photopolymerizable compounds used contains an alkali-soluble group. In addition to initiation of crosslinking polymerization, this type of compound should be soluble for a developing solution (a common alkali developer) used in the procedure of development treatment when an image pattern is formed, preferably carboxyl-containing resin, particularly a (meth) acrylate-based polymer formed by copolymerization of a (meth)acrylate, an ethylenically unsaturated carboxylic acid, and a further copolymerizable monomer. The (meth)acrylate may be methyl (meth)acrylate, ethyl (meth)acrylate, butyl (meth)acrylate, cyclohexyl (meth)acrylate, benzyl (meth) acrylate, diethylaminoethyl (meth)acrylate, dimethylaminoethyl (meth)acrylate, hydroxyethyl (meth)acrylate, hydroxypropyl (meth)acrylate, furfuryl (meth)acrylate, or glycidyl (meth)acrylate. As for these (meth)acrylates, one kind may be used alone, or two or more kinds may be used in combination. The ethylenically unsaturated carboxylic acid is preferably acrylic acid, methacrylic acid, vinylbenzoic acid, maleic acid, alkyl maleate, fumaric acid, itaconic acid, butenic acid, cinnamic acid, an acrylic acid dimer, an addition product of a monomer having a hydroxy group (for example, 2-hydroxyethyl (meth)acrylate, etc.) and a cyclic acid anhydride (for example, maleic anhydride, phthalic anhydride, and cyclohexenedicarboxylic anhydride), or an ω-carboxyl-polycaprolactone-(meth)acrylate. In view of copolymerizability, cost, and solubility, (meth)acrylic acids are particularly preferably. As for these ethylenically unsaturated carboxylic acids, one kind may be used alone, or two or more kinds may be used in combination. The further copolymerizable monomer is preferably (meth)acrylamide, n-butyl (meth)acrylate, styrene, vinylnaphthalene, (meth) acrylonitrile, vinyl acetate, or vinylcyclohexane. As for these monomers, one kind may be used alone, or two or more kinds may be used in combination.

As for these carbon-carbon double bond compounds, one kind may be used alone, two or more kinds may be used in combination, or pre-copolymerization may be performed on a mixture to form an oligomer for formulating a composition for use. The usage amount of radical polymerizable resin present in the photocurable composition is 5-95 parts by mass, preferably about 10-90 parts by mass.

2) Photoinitiator Having Structure Represented by General Formula (I)

The photoinitiator used in the photocurable composition of the present invention at least includes one of compounds having a fluorene-based compound represented by general formula (I) as a main structure or derivative compounds thereof:

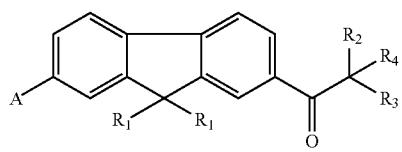
(I)

wherein,

A represents hydrogen, a halogen, a nitro group, a $C_1$-$C_{20}$ linear or branched alkyl group, a $C_3$-$C_{10}$ alkylcycloalkyl group, a $C_4$-$C_{10}$ alkylcycloalkyl or cycloalkylalkyl group,

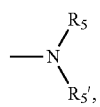

—$COR_6$, or a —CO—$CR_2R_3R_4$ group, wherein, optionally, —$CH_2$— is substituted with O, N, S, or C(=O);

$R_1$ represents hydrogen, a halogen, a $C_1$-$C_{20}$ linear or branched alkyl group, a $C_4$-$C_{20}$ cycloalkylalkyl group, or a $C_2$-$C_{20}$ alkenyl group, wherein, optionally, —$CH_2$— in $R_1$ is substituted with O, N, S, or C(=O), and a ring may be formed between $R_1$s, $R_2$ and $R_3$ each independently represent a $C_1$-$C_{20}$ linear or branched alkyl group, a $C_3$-$C_{20}$ cycloalkyl group, a $C_4$-$C_{20}$ cycloalkylalkyl group, a $C_4$-$C_{20}$ alkylcycloalkyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in $R_2$ and $R_3$ is substituted with O, N, S, or C(=O), and $R_2$ and $R_3$ may be linked to each other to form a ring;

or $R_2$ represents a $C_1$-$C_{20}$ linear or branched alkyl group or a $C_2$-$C_{20}$ alkenyl group, and $R_3$ is selected from any one of following groups:
a) a group having a chemical formula as follows:

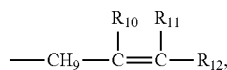

wherein m is 0 or 1, $R_9$ represents hydrogen, a $C_1$-$C_8$ alkyl group, or a phenyl group, and $R_{10}$, $R_{11}$, and $R_{12}$ each independently represent hydrogen or a $C_1$-$C_4$ alkyl group; or
b) a group having a chemical formula as follows:

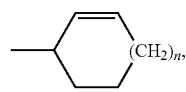

wherein n is 0, 1, 2, or 3; or
c) a group having a chemical formula as follows:

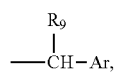

wherein Ar is a substituted or unsubstituted phenyl, naphthyl, furanyl, thienyl, or pyridinyl group;

$R_4$ represents a N-morpholinyl group, a N-piperidinyl group, a N-pyrrolyl group, or a N-dialkyl group, wherein one or more hydrogen atoms in these groups may be substituted with a halogen or a hydroxy group;

$R_5$ and $R_5'$ each independently represent a $C_1$-$C_{20}$ linear or branched alkyl group, a $C_4$-$C_{20}$ cycloalkyl group, a $C_2$-$C_{20}$ alkenyl group, a $C_6$-$C_{20}$ aryl group, or a $C_6$-$C_{20}$ alkylaryl group, wherein one or more hydrogen atoms in these groups may be each independently substituted with an alkyl group, a halogen, a hydroxy group, or a nitro group, and optionally, —$CH_2$— in these groups may be substituted with —O—; or $R_5$ and $R_5'$ may form a five-membered or six-membered ring by being linked to each other or via —O—, —S—, or —NH—;

$R_6$ represents a $C_1$-$C_{20}$ linear or branched alkyl group, a $C_4$-$C_{20}$ cycloalkyl group, a $C_4$-$C_{20}$ alkylcycloalkyl group, a $C_2$-$C_{20}$ alkenyl group, a $C_6$-$C_{20}$ aryl group, or a $C_6$-$C_{20}$ alkylaryl group, wherein —$CH_2$— in these groups may be substituted with —O— or —S—, and one or more hydrogen atoms in these groups may be independently substituted with a group selected from an alkyl group, a halogen, a nitro group, a cyano group, $SR_7$, and $OR_8$;

$R_7$ and $R_8$ each independently represent hydrogen or a $C_1$-$C_{20}$ linear or branched alkyl group.

As a preferable embodiment, the fluorenylaminoketone compound represented by formula (I) includes compounds represented by the following structures:

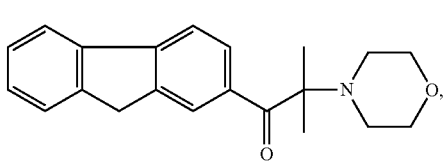
Compound 1

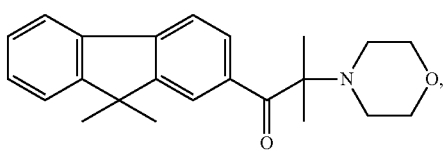
Compound 2

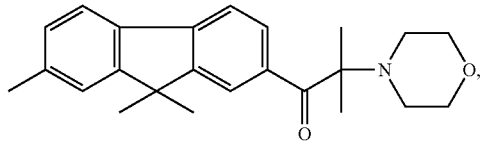
Compound 3

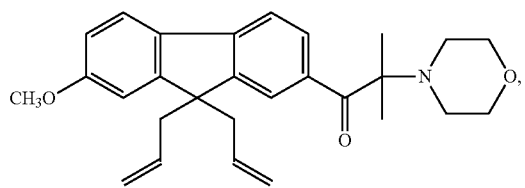
Compound 4

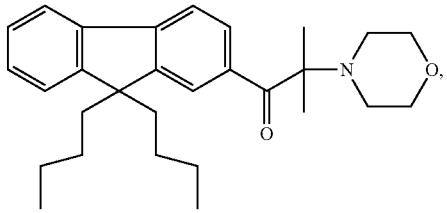
Compound 5

Compound 6
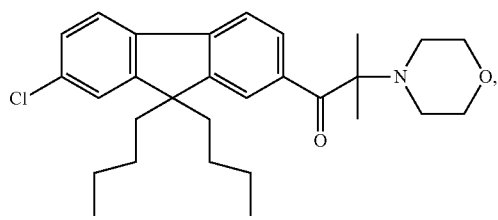
Compound 7
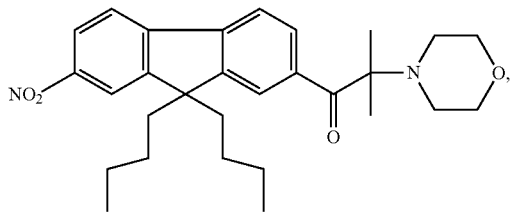
Compound 8
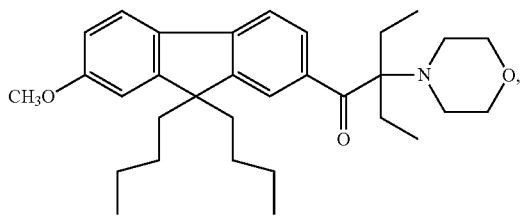
Compound 9
Compound 10
Compound 11
Compound 12
Compound 13
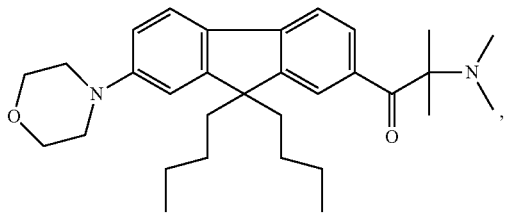
Compound 14
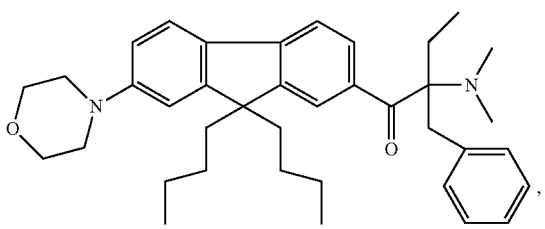
Compound 15
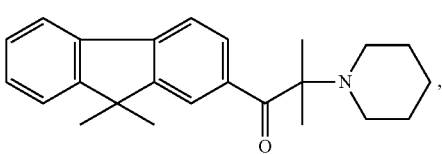
Compound 16
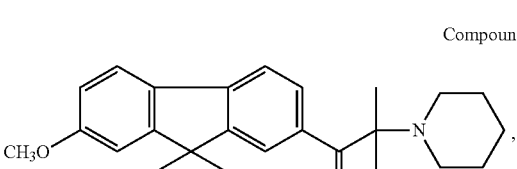
Compound 17
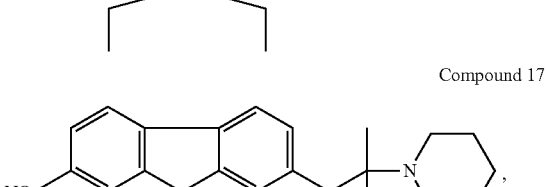
Compound 18
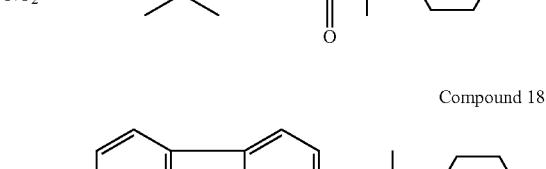
Compound 19
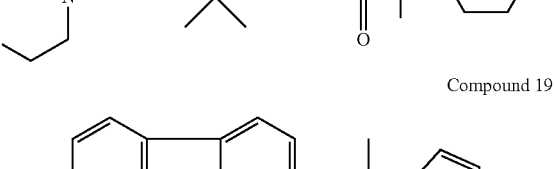

Compound 20
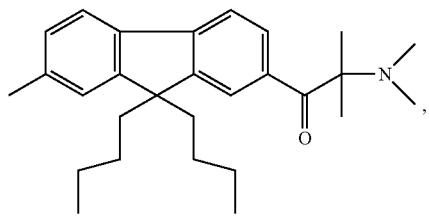
Compound 21
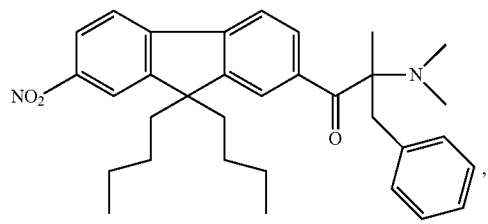
Compound 22
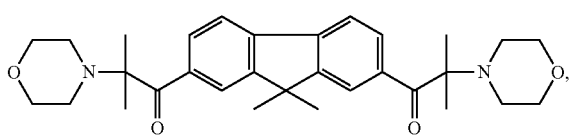
Compound 23
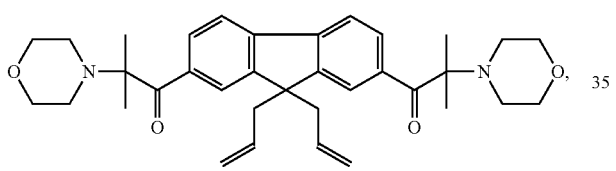
Compound 24
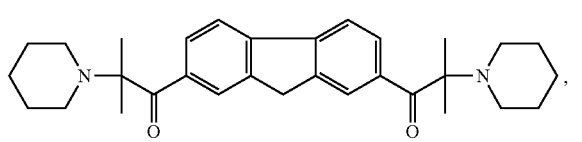
Compound 25
Compound 26
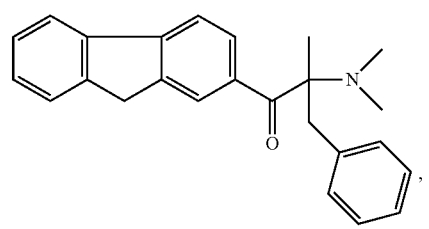
Compound 27
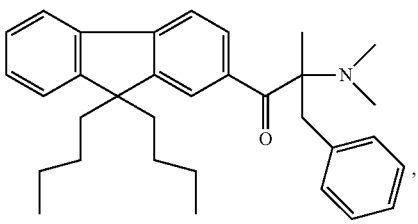
Compound 28
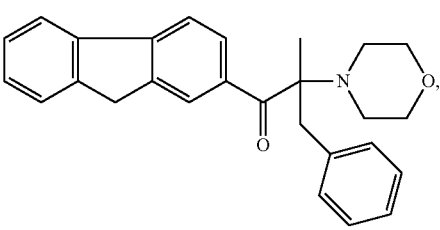
Compound 29
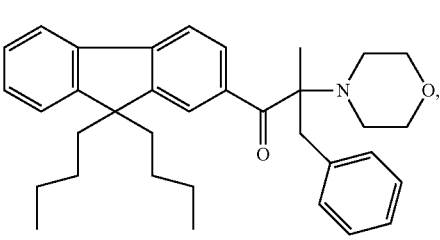
Compound 30
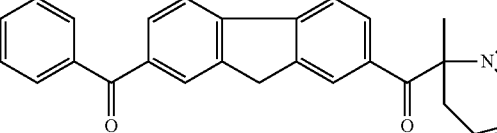
Compound 31
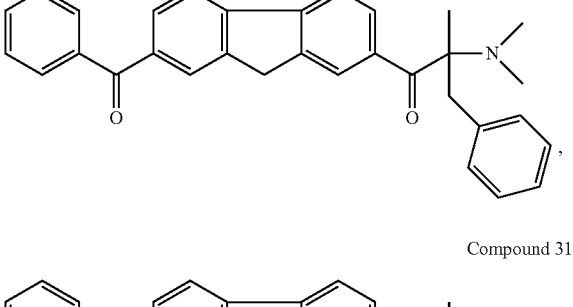
Compound 32
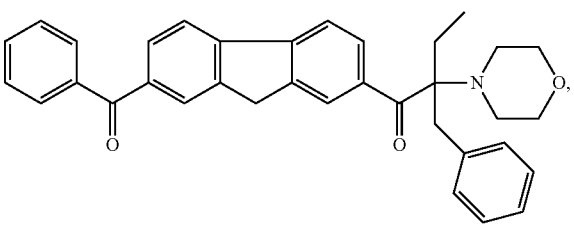

Compound 33

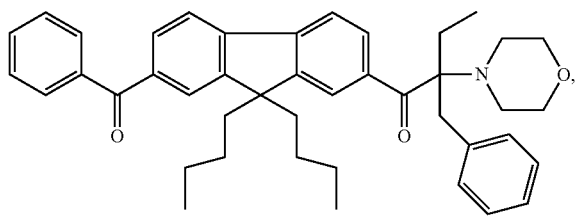

Compound 34

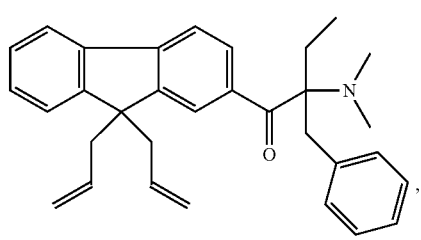

Compound 35

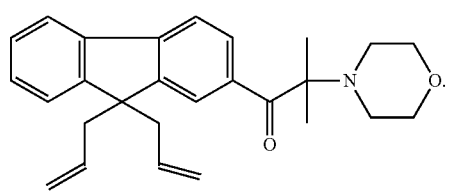

The derivative compound having the compound represented by formula (I) as a main structure refers to a derivative obtained by maintaining a main structure of a compound of formula (I) unchanged while allowing branch chain(s) thereof to be substituted or linked to each other. When used as a photoinitiator in the present invention, the derivative compound having the compound represented by formula (I) as the main structure is the compound represented by the following formula (II) or (III):

optionally, —$CH_2$— in M is substituted with sulfur, oxygen, NH, or a carbonyl group, and optionally, a hydrogen atom is substituted with OH or $NO_2$.

Exemplarily, the derivative compound described above may be compounds having the following structures:

Compound 36

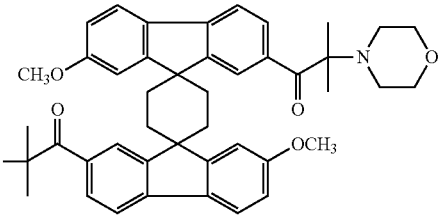

Compound 37

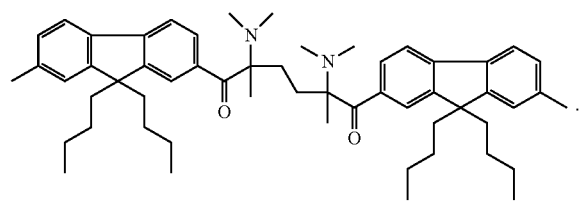

In some cases, it is advantageous to use a mixture of two or more of the initiators described above.

Of course, the photoinitiator having a structure represented by general formula (I) may also be mixed and used with any other known photoinitiator.

3) Another Photoinitiator

Examples include camphorquinone; benzophenone (BP); benzophenone derivatives, for example 2,4,6-trimethylbenzophenone, 2-methylbenzophenone, 2-methylbenzophenone, 3-methylbenzophenone, 4-methylbenzophenone, 2-methylcarbonylbenzophenone, 4,4'-bis(chloromethyl)benzophenone, 4-chlorobenzophenone, 4-phenylbenzophenone, 3,3'-dimethyl-4-methoxy-benzophenone, [4-(4-methylphenylthio)phenyl]-phenyl methanone, methyl 2-benzoylbenzoate, 3-methyl-4'-phenylbenzophenone, 2,4,6-trimethyl-4'-phenylbenzophenone, 4,4'-bis(dimethylamino)benzophenone, and 4,4'-bis(diethylamino)benzophenone; ketal compounds, for example benzildimethyl ketal

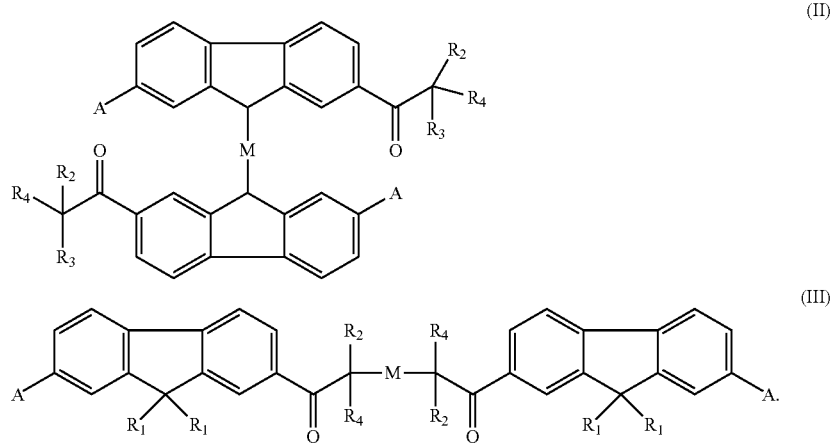

Formula (II) and formula (III) are dimers of formula (I), wherein M represents a linking group formed by dimerization and may be absent, a $C_1$-$C_{10}$ linear or branched alkylene group, or a $C_6$-$C_{12}$ arylene or heteroarylene group, and (651); acetophenone; acetophenone derivatives, for example alpha-hydroxycycloalkyl phenyl ketone, such as 2-hydroxy-2-methyl-1-phenyl-acetone (1173), 1-hydroxy-cyclohexyl-phenyl-one (184), 1-[4-(2-hydroxyethoxy)-phenyl]-2-hydroxy-2-methyl-1-propan-1-one (2959), 2-hydroxy-1-{4-[4-(2-hydroxy-2-methyl-propionyl)-benzyl]-phenyl}-2-methyl-propan-1-one (127), and 2-hydroxy-1-{4-[4-(2-hydroxy-2-methyl-propionyl)-phenoxy]-yl}-2-methyl-propan-1-one; dialkoxyacetophenone; alpha-hydroxyacetophenone or alpha-aminoacetophenone, for example (4-methylthiobenzoyl)-1-methyl-1-morpholinoethane (907), (4-morpholinobenzoyl)-1-benzyl-1-dimethylaminopropane (369), (4-morpholinobenzoyl)-1-(4-methylbenzyl)-1-dimethylaminopropane (379), (4-(2-hydroxyethyl) amino benzoyl)-1-benzyl-1-dimethylaminopropane), and 2-benzyl-2-dimethylamino-1-(3,4-dimethoxyphenyl)-1-butanone; thioxanthone and derivatives thereof, for example isopropylthioxanthene (ITX), 2-chlorothioxanthone (CTX), 1-chloro-4-propoxythioxanthone (CPTX), and 2,4-diethyl-thioxanthone (DETX); benzoin alkyl ethers and benzil ketals; phenyl glyoxylate and derivatives thereof, for example 2-(2-hydroxy-ethoxy)-ethyl oxo-phenyl-acetate; dimerized phenyl glyoxylate, for example 1-methyl-2-[2-(2-oxo-phenylacetoxy)-propoxy]-ethyl oxo-phenyl-acetate (754); other oxime esters, for example 1,2-octanedione-1-[4-(phenyl-thio)phenyl]-2-(4-benzoyloxime) (OXE01), ethanone-1-[9-ethyl-6-(2-methyl benzoyl)-9H-carbazol-3-yl]-1-(4-acetyloxime) (OXE02), and 9H-thioxanthene-2-carboxaldehyde-9-oxo-2-(O-acetyloxime); monoacylphosphine oxide, for example (2,4,6-trimethyl-benzoyl)diphenylphosphine oxide (TPO); diacylphosphine oxide, for example bis-(2,6-dimethoxy-benzoyl)-(2,4,4-trimethyl-pentyl)phosphine oxide, bis(2,4,6-trimethylbenzoyl)-phenylphosphine oxide (819), and bis(2,4,6-trimethylbenzoyl)-2,4-dipentoxyphenyl-phosphine oxide; hexaaryl bisimidazole/coinitiator systems, for example o-chlorohexaphenylbisimidazole in combination with 2-mercaptobenzothiazole, etc.

It is to be noted that photoinitiators having structures represented by general formula (I), in addition to the compounds of formula (I), formula (II), and formula (III), are particularly suitable to be used in combination with one or more of BP, 651, 1173, 184, ITX, TPO, 819, etc. The usage amount of the photoinitiator which is the photoinitiator having a structure represented by general formula (I) and another photoinitiator in the photocurable composition is 0.05-15 parts by mass, preferably 1-10 parts by mass.

4) Sensitizer

Furthermore, the photocurable composition of the present invention may also further comprise a sensitizer in order to obtain a higher sensitivity or in order to match an LED light source.

The type of the sensitizer may be a pyrazoline compound, an acridine compound, an anthracene compound, a coumarin compound, a tertiary amine compound, etc. Specifically, the following may be exemplarily listed: 1-phenyl-3-(4-tert-butylstyryl)-5-(4-t-butylphenyl)pyrazoline, and 1-phenyl-3-biphenyl-5-(4-t-butylphenyl)pyrazoline; 9-phenylacridine, 9-p-methyl phenylacridine, 9-m-methyl phenylacridine, and 9-o-chloro phenylacridine; 2-ethylanthracene-9,10-di (methyl 4-chlorobutyrate), 1,2,3-trimethylanthracene-9,10-dioctyl ester, 2-ethylanthracene-9,10-diethyl ester, 2-ethylanthracene-9,10-di(3-cyclohexyl propionate); 3,3'-carbonylbis(7-diethylaminocoumarin), 3-benzoyl-7-diethylaminocoumarin, 3,3'-carbonylbis(7-methoxycoumarin), 7-(diethylamino)-4-methylcoumarin; N,N-bis-[4-(2-styryl-1-yl)-phenyl]-N,N-bis(2-ethyl-6 methylphenyl)-1,1-bis phenyl-4,4-diamine, N,N-bis-[4-(2-styryl-1-yl)-4'-methylphenyl]-N,N-bis(2-ethyl-6 methylphenyl)-1,1-bis phenyl-4,4-diamine, etc.

The usage amount of the sensitizer in the photocurable composition is 0-5 parts by mass, preferably 0-2 parts by mass.

5) Colorant

The UV photocurable composition may comprise one or more pigments as a colorant. The pigment may be of any color, including but not limited to, black, blue, brown, cyan, green, white, purple, magenta, red, orange, and yellow, as well as a spot color of a mixture thereof. The pigment may be an inorganic pigment or an organic pigment.

The organic pigment present in the UV photocurable composition may be perylene, a phthalocyanine pigment (for example, phthalocyanine green and phthalocyanine blue), a cyanine pigment (Cy3, Cy5, and Cy7), a naphthalocyanine pigment, a nitroso pigment, an azo pigment, an diazo pigment, a diazo condensation pigment, a basic dye pigment, a basic blue pigment, an indigo pigment, a phloxin pigment, a quinacridone pigment, an isoindolinone pigment, a dioxazine pigment, a carbazole dioxazine violet pigment, a alizarin lake pigment, a polyphthalamide pigment, a carmine lake pigment, a tetrachloroisoindolinone pigment, a perynone pigment, an anthraquinone pigment, and a quinophthalone pigment, as well as a mixture of two or more thereof or a derivative thereof.

The inorganic pigment in the photocurable composition includes, for example, a metal oxide (for example, titanium dioxide, conductive titanium dioxide), an iron oxide (for example, red iron oxide, yellow iron oxide, black iron oxide, and transparent iron oxide), an aluminum oxide, a silicon oxide, a carbon black pigment, a metal sulfide, a metal chloride, and a mixture of two or more thereof.

The usage amount of the colorant in the photocurable composition is 0-50 parts by mass, preferably 0-20 parts by mass.

6) Additive

According to requirements for various applications various, other components or additives may be optionally present in the photocurable composition to improve properties and performances of coatings or inks. The additive includes but is not limited to one or more of a surfactant, a wetting agent, a dispersant, a rheology modifier, a defoamer, and a storage enhancer.

The usage amount of the additive in the photocurable composition is 0-5 parts by mass, preferably 0-3 parts by mass.

The polymer of interest may be obtained by polymerizing the photocurable composition of the present invention in polymerization reaction by giving the energy generated by ultraviolet, visible light, near infrared, electron beams, and the like. As a light source for giving the energy, light sources having the dominant wavelength which emits light in a wavelength region of 250 nm to 450 nm are preferable. As the light source having the dominant wavelength which emits light in a wavelength region of 250 nm to 450 nm, various light sources may be exemplified, such as ultrahigh-pressure mercury lamps, high-pressure mercury lamps, medium-pressure mercury lamps, mercury-xenon lamps, metal halide lamps, large-power metal halide lamps, xenon lamps, pulse light-emitting xenon lamps, deuterium lamps, Led lamps, fluorescent lamps, Nd-YAG triple wave laser, He—Cd laser, nitrogen laser, Xe—Cl excimer laser, Xe—F excimer laser, semiconductor-excited solid laser, and the like.

The present invention will be specifically illustrated by Examples, but it is to be understood that the Examples should not be construed to be limitations of the present invention. The person skilled in the art is fully capable of amending the Examples illustrated in the framework of the present invention to obtain the same or similar effect.

Example 1

(1) Preparation of 9,9-dimethyl-7-fluorofluorene-2-butanone (Intermediate 38a)

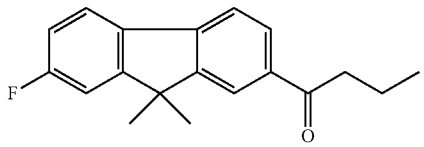 [SMILES: CCCC(=O)c1ccc2c(c1)C(C)(C)c1cc(F)ccc1-2]

80 g of anhydrous aluminum trichloride, 106 g of 9,9-dimethyl-7-fluorofluorene, and 150 ml of a dichloromethane solvent were added to a 500 ml four-neck flask, the temperature was controlled at 10° C. or less, 53 g of n-butanoyl chloride was slowly dropped, and the temperature was increased to 35-45° C. after the addition was finished, followed by stirring for 4-6 h. The reactant was cooled and then poured into hydrochloric acid-ice water to separate an organic layer, which was washed until it was neutral and dried, and reduced-pressure distillation was performed to obtain 109 g of an intermediate 38a, with a yield of 78% and a purity of 99%. MS (m/z): 283 (M+1)+.

(2) Preparation of 2-chloro-9,9-dimethyl-7-fluorofluorene-1-butanone (Intermediate 38b)

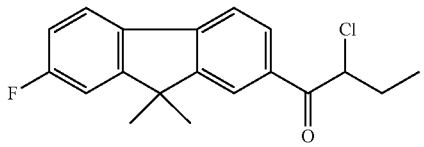 [SMILES: CCC(Cl)C(=O)c1ccc2c(c1)C(C)(C)c1cc(F)ccc1-2]

141 g of the intermediate 38a and 100 ml of a dichloromethane solvent were added to a four-neck flask, the temperature was controlled at 30-40° C. and 59 g of thionyl chloride was dropped, nitrogen gas was introduced to remove hydrogen chloride. An organic layer was separated by washing with water and dried, and the solvent was recovered to obtain 147 g of an intermediate 38b, with a yield of 93% and a purity of 98%. MS (m/z): 317 (M+1)+.

(3) Preparation of 2-dimethylamino-9,9-dimethyl-7-fluorofluorene-1-butanone (Intermediate 38c)

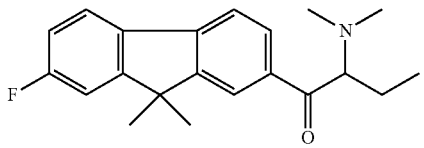 [SMILES: CCC(C(=O)c1ccc2c(c1)C(C)(C)c1cc(F)ccc1-2)N(C)C]

An ethyl ether solution containing 75 g dimethylamine was added to a four-neck flask and placed in an ice bath, 158 g of the intermediate 38b was dropped with stirring, the temperature was controlled at about 0° C., and reaction was performed with stirring. Nitrogen gas was introduced to remove excess of dimethylamine. The reaction liquid was poured into water to separate an organic layer, which was washed with water until it was neutral and dried to distill off ethyl ether, and reduced-pressure distillation was performed to obtain 133 g of an intermediate 38c, with a yield of 82% and a purity of 99%. MS (m/z): 326 (M+1)+.

(4) Preparation of 2-benzyl-2-dimethylamino-9,9-dimethyl-7-fluorofluorene-1-butanone (Intermediate 38d)

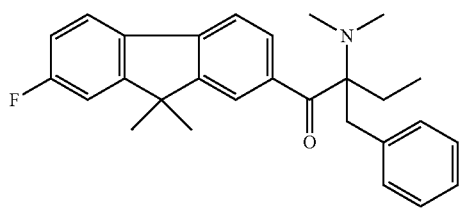 [SMILES: CCC(Cc1ccccc1)(C(=O)c1ccc2c(c1)C(C)(C)c1cc(F)ccc1-2)N(C)C]

162 g of the intermediate 38c and 150 ml of a toluene solvent were added to a four-neck flask, and 63 g of benzyl chloride was slowly dropped, followed by increasing temperature and stirring for 12 h. The solvent was recovered by distillation, water was added, and the temperature was increased to 50-70° C., and an alkaline liquor was added to perform reflux reaction for 0.5-1 h. After cooling, an organic layer was separated, a yellow viscous substance was obtained by extraction and drying, and recrystallization was performed with ethanol to obtain 193 g of an intermediate 38d, with a yield of 93% and a purity of 97%. MS (m/z): 416 (M+1)+.

(5) Preparation of 2-benzyl-2-dimethylamino-9,9-dimethyl-1-(7-morpholinofluorenyl)butanone (Compound 38)

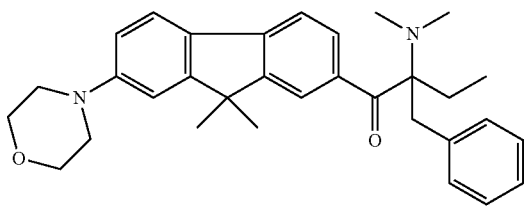 [SMILES: CCC(Cc1ccccc1)(C(=O)c1ccc2c(c1)C(C)(C)c1cc(N3CCOCC3)ccc1-2)N(C)C]

103 g of the intermediate 38d, 45 g of morpholine, 100 ml of a DMSO solvent, and 5 g of potassium carbonate were sequentially added to a four-neck flask, and the temperature was increased to 120-160° C. to perform reaction for 30 h. After cooling, a reddish brown paste was obtained by extraction, washing, and drying, and recrystallization was performed with ethanol to obtain 89 g of a compound 38 after drying, with a yield of 75% and a purity of 99.5%.

The structure of the product was determined by hydrogen nuclear magnetic resonance spectroscopy and mass spectrometry.

$^1$H-NMR (CDCl$_3$, 500 MHz): 0.96-1.54 (5H, m), 1.67 (6H, s), 2.27 (6H, s), 2.76 (2H, s), 2.92 (4H, m), 3.67 (4H, m), 6.71-7.66 (8H, m), 7.92-8.18 (3H, m).

MS (m/z): 483 (M+1)$^+$.

Example 2

(1) Preparation of 2-allyl-2-dimethylamino-9,9-dimethyl-7-fluorofluorene-1-butanone (Intermediate 39d)

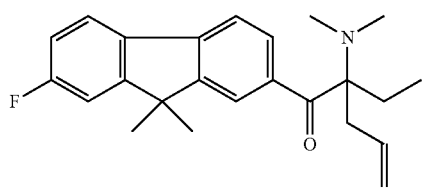 [SMILES: C=CCC(CC)(C(=O)c1ccc2c(c1)C(C)(C)c1cc(F)ccc1-2)N(C)C]

With the intermediate 38c in Example 1 as a raw material, 162 g of 38c and an appropriate amount of toluene solvent were added to a four-neck flask, and 39 g of allyl chloride was slowly dropped, followed by increasing temperature and stirring for 12 h. The solvent was recovered by distillation, water was added, and the temperature was increased to 50-70° C., and an alkaline liquor was added to perform reflux reaction for 0.5-1 h. After cooling, an organic layer was separated, a yellow viscous substance was obtained by extraction and drying, and recrystallization was performed with ethanol to obtain 167 g of an intermediate 39d, with a yield of 92% and a purity of 98%. MS (m/z): 366 (M+1)$^+$.

(2) Preparation of 2-allyl-2-dimethylamino-9,9-dimethyl-2-(7-piperidinylfluorenyl)butanone (Compound 39)

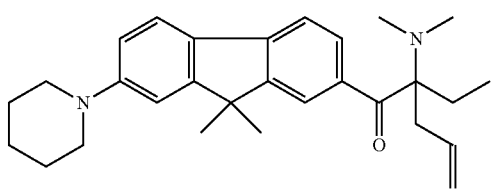 [SMILES: C=CCC(CC)(C(=O)c1ccc2c(c1)C(C)(C)c1cc(N3CCCCC3)ccc1-2)N(C)C]

92 g of the intermediate 39d, 45 g of piperidine, an appropriate amount of DMSO solvent, and a small amount of potassium carbonate were sequentially added to a four-neck flask, and the temperature was increased to 120-160° C. to perform reaction for 30 h. After cooling, a reddish brown paste was obtained by extraction, washing, and drying, and recrystallization was performed with ethanol to obtain 83 g of a compound 39 after drying, with a yield of 73% and a purity of 99%.

The structure of the product was determined by hydrogen nuclear magnetic resonance spectroscopy and mass spectrometry.

$^1$H-NMR (CDCl$_3$, 500 MHz): 0.96-1.54 (11H, m), 1.67 (6H, s), 2.17 (2H, s), 2.27 (6H, s), 2.72 (4H, m), 4.97-5.71 (3H, m), 6.71-8.18 (6H, m).

MS (m/z): 431 (M+1)$^+$.

Example 3

(1) Preparation of 9,9-dibutylfluorene-1-butanone (Intermediate 40a)

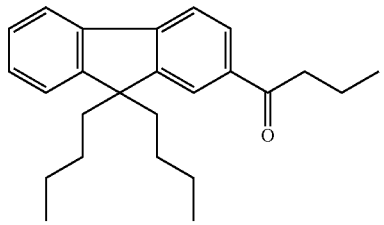 [SMILES: CCCCC1(CCCC)c2ccccc2-c2ccc(C(=O)CCC)cc21]

The method was the same as the preparation method of 38a. MS (m/z): 349 (M+1)$^+$.

(2) Preparation of 2-chloro-9,9-dibutylfluorene-1-butanone (Intermediate 40b)

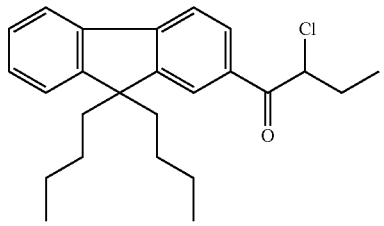 [SMILES: CCCCC1(CCCC)c2ccccc2-c2ccc(C(=O)C(Cl)CC)cc21]

The method was the same as the preparation method of 38b. MS (m/z): 383 (M+1)$^+$.

(3) Preparation of 2-dimethylamino-9,9-dibutylfluorene-1-butanone (Intermediate 40c)

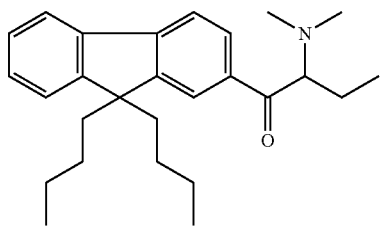 [SMILES: CCCCC1(CCCC)c2ccccc2-c2ccc(C(=O)C(CC)N(C)C)cc21]

The method was the same as the preparation method of 38c. MS (m/z): 392 (M+1)$^+$.

(4) Preparation of 2-benzyl-2-dimethylamino-9,9-dibutylfluorene-1-butanone (Compound 40)

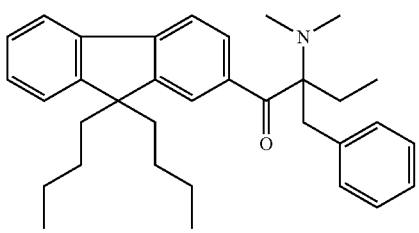 [SMILES: CCCCC1(CCCC)c2ccccc2-c2ccc(C(=O)C(CC)(Cc3ccccc3)N(C)C)cc21]

The method was the same as the preparation method of 38d.

The structure of the product was determined by hydrogen nuclear magnetic resonance spectroscopy and mass spectrometry.

$^1$H-NMR (CDCl$_3$, 500 MHz): 0.96-1.87 (23H, m), 2.27 (6H, s), 2.76 (2H, s), 7.08-8.18 (12H, m).

MS (m/z): 482 (M+1)$^+$.

Example 4

(1) Preparation of 2-benzyl-2-dimethylamino-9,9-dibutyl-1-(7-benzoyl)butanone (Compound 41)

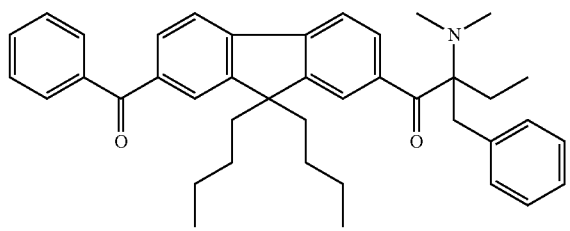 [SMILES: CCCCC1(CCCC)c2cc(C(=O)c3ccccc3)ccc2-c2ccc(C(=O)C(CC)(Cc3ccccc3)N(C)C)cc21]

80 g of anhydrous aluminum trichloride, 240.5 g of a compound 3, and 200 ml of a dichloromethane solvent were added to a 1000 ml four-neck flask, the temperature was controlled at 10° C. or less, 70 g of benzoyl chloride was slowly dropped, and the temperature was increased to 35-45° C. after the addition was finished, followed by stirring for 4-6 h. The reactant was cooled and then poured into hydrochloric acid-ice water to separate an organic layer, which was washed until it was neutral and dried, and reduced-pressure distillation was performed to obtain 237 g of an intermediate compound 39, with a yield of 81% and a purity of 98%.

The structure of the product was determined by hydrogen nuclear magnetic resonance spectroscopy and mass spectrometry.

$^1$H-NMR (CDCl$_3$, 500 MHz): 0.96-1.87 (23H, m), 2.27 (6H, s), 2.76 (2H, s), 7.08-8.18 (16H, m).

MS (m/z): 586 (M+1)$^+$.

Examples 5-20

Compounds 42-57 of Examples 5-20 were prepared with reference to the synthesis methods of Examples 1-4. That is, the compound prepared in Example 5 was compound 42, the compound prepared in Example 6 was compound 43, and so on. Compounds of interest and LC-MS data thereof were listed in Table 1.

TABLE 1

| Compound | R$_1$ | R$_2$ | R$_3$ | X | Y | MS (m/z) |
|---|---|---|---|---|---|---|
| Compound 42 | —CH$_3$ | —C$_2$H$_5$ | —CH$_2$C$_6$H$_5$ | —N(CH$_3$)$_2$ | —N(C$_4$H$_9$)$_2$ | 525 |
| Compound 43 | —CH$_2$CH$_2$CH$_3$ | —C$_2$H$_5$ | —CH$_2$C$_6$H$_5$ | —N(CH$_3$)$_2$ | piperidinyl | 537 |
| Compound 44 | —CH$_3$ | —C$_2$H$_5$ | —CH$_2$-C$_6$H$_4$-CH$_3$ | piperidinyl | piperidinyl | 535 |
| Compound 45 | —CH$_3$ | —C$_2$H$_5$ | —CH$_2$C$_6$H$_5$ | —N(CH$_3$)$_2$ | —N(CH$_2$CH$_2$OH)$_2$ | 501 |
| Compound 46 | —CH$_3$ | —CH$_3$ | —CH$_2$C$_6$H$_5$ | piperidinyl | morpholinyl | 509 |
| Compound 47 | —CH$_2$CH$_2$CH$_3$ | —C$_2$H$_5$ | —CH$_2$-C$_6$H$_4$-CH$_3$ | piperidinyl | morpholinyl | 593 |

TABLE 1-continued

| Compound | R₁ | R₂ | R₃ | X | Y | MS (m/z) |
|---|---|---|---|---|---|---|
| Compound 48 | —H | —C₂H₅ | 4-chlorobenzyl | piperidinyl | morpholinyl | 530 |
| Compound 49 | —H | —C₂H₅ | 4-methylbenzyl | —N(CH₃)₂ | morpholinyl | 469 |
| Compound 50 | cyclohexylmethyl | —C₂H₅ | benzyl | —N(CH₃)₂ | morpholinyl | 648 |
| Compound 51 | —CH₃ | —C₂H₅ | —CHCH=CH₂ | piperidinyl | morpholinyl | 473 |
| Compound 52 | —CH₃ | —CHCH=CH₂ | —CHCH=CH₂ | —N(CH₃)₂ | morpholinyl | 445 |
| Compound 53 | —CH₂CH₂CH₃ | —CH₃ | 4-methylbenzyl | morpholinyl | 3,5-dimethylmorpholinyl | 609 |
| Compound 54 | —H | —C₂H₅ | 4-isopropyl-3-methylbenzyl | piperidinyl | —N(CH₂OCH₂CH₃)₂ | 555 |
| Compound 55 | —H | —C₂H₅ | benzyl | morpholinyl | —H | 412 |
| Compound 56 | —H | —C₂H₅ | benzyl | morpholinyl | benzoyl | 516 |
| Compound 57 | —CH₂CH₂CH₂CH₃ | —C₂H₅ | benzyl | morpholinyl | benzoyl | 628 |

Evaluation of Properties

1. Test of Solubility Property

By taking a diluent 1,6-hexanediol diacrylate (HDDA) and an acetone solvent, which were widely used in the art, as examples, solubility properties of the photoinitiator of the present invention and Irgacure 369 and Irgacure 379 as mentioned in the background art were tested, and the largest weight which could be dissolved in 100 g of a solvent under a condition of 20° C. as an evaluation criterion. Test results were as shown in Table 2.

TABLE 2

| Example/Comparative Example | Sample | HDDA (g/100 g) | Acetone (g/100 g) |
|---|---|---|---|
| Example | Compound 4 | >15 | >30 |
| | Compound 5 | >15 | >30 |
| | Compound 9 | >15 | >30 |
| | Compound 14 | >15 | >30 |
| | Compound 24 | >15 | >30 |
| | Compound 34 | >15 | >30 |
| | Compound 38 | >15 | >30 |
| | Compound 39 | >15 | >30 |
| | Compound 40 | >15 | >30 |
| | Compound 41 | >15 | >30 |
| | Compound 42 | >15 | >30 |
| | Compound 43 | >15 | >30 |
| | Compound 44 | >15 | >30 |
| | Compound 45 | >15 | >30 |
| | Compound 46 | >15 | >30 |
| | Compound 47 | >15 | >30 |
| | Compound 48 | >15 | >30 |
| | Compound 49 | >15 | >30 |
| | Compound 50 | >15 | >30 |
| | Compound 51 | >15 | >30 |
| | Compound 52 | >15 | >30 |
| | Compound 53 | >15 | >30 |
| | Compound 54 | >15 | >30 |
| | Compound 55 | >15 | >30 |
| | Compound 56 | >15 | >30 |
| | Compound 57 | >15 | >30 |
| Comparative Example | Irgacure 369 | 5 | 17 |
| | Irgacure 379 | 11 | 24 |

As could be seen from Table 2, compared to commercial photoinitiators Irgacure 369 and Irgacure 379, the solubility of the alpha-aminoketone photoinitiator of the present invention containing a fluorene structure was greatly improved, and the use of micromolecular active diluent could be reduced to a very large extent when the photoinitiator of the present invention was used.

2. Test of Curing Property

The alpha-aminoketone photoinitiator had a very high photoinitiator activity in a photocurable colored system and was particularly suitable for photocurable paints and inks. Therefore, this initiator was used in an ink system to evaluate the curing property.

Step 1: The preparation of a color paste, wherein weight percentages of components in the color paste were as shown below:

| Composition | Yellow | Red | Blue | Black |
|---|---|---|---|---|
| Pigment component | Benzidine yellow | Permanent red | Phthalocyanine blue | Carbon black |
| Pigment content (%) | 10 | 10 | 10 | 10 |
| 1,6-hexanediol diacrylate (%) | 40 | 40 | 40 | 40 |
| trimethylolpropane triacrylate (%) | 47 | 47 | 47 | 47 |
| EFKA-4310 dispersant (%) | 3 | 3 | 3 | 3 |

The raw material components described above were ground with a sitting-type sand mill to a particle size of <1 μm, followed by filtration to obtain the color paste.

Step 2: The preparation of an ink for UV curing, in which weight proportions of components in the ink were as shown below:

| | |
|---|---|
| Urethane acrylate SR9010 | 70% |
| Epoxy acrylate E201 | 20% |
| The color paste | 2% |
| Photoinitiator | 5% |
| ITX | 2% |
| Leveling agent | 0.5% |
| Silane coupling agent | 0.5% |
| Butanone | Present or absent (adjusted according to the solubility of the initiator) |

The photoinitiator in the components of the ink described above was the photoinitiator of the present invention or commercial photoinitiators Irgacure 369 and Irgacure 907. Since 369 had a relatively poor solubility, about 10% of the butanone solvent was required to be added to the formulation described above to allow it to be completely dissolved.

The formulation described above was stirred in a four-neck flask at room temperature under protection from light for 3 h, followed by filtration to obtain an ink for curing. The ink was spray coated on a ceramic tile with a spray coating thickness of 60-80 μm, and then irradiated with ultraviolet of an ultraviolet light source having a power of 80 mw/cm² for 50s. The ceramic tile after being ultraviolet cured was then placed at 80° C. to sinter for 50 min, and the effect of the ink coating layer on the ceramic tile was detected after cooling.

Here, tests of adherence were performed by using a hundred-grid crosscut method and evaluation was performed according to criteria of 0-5 levels, with reference to GB/T 9286-1998 test standard. The deep-layer curing degree was tested by a finger scratch method, in which a coating layer was scratched with a fingernail and complete curing of the bottom layer was indicated by no phenomenon of peeling-off or exposed bottom. The pattern effect was visually observed, wherein a clear and fine pattern having a smooth edge without burrs was defined as a criterion of a good pattern effect. Specific test results were as shown in Table 3, Table 4, Table 5, and Table 6.

TABLE 3

Test results of yellow ink

| Example/Comparative Example | Compound | Adherence | Deep-layer curing degree | Pattern effect |
|---|---|---|---|---|
| Example | Compound 4 | Level 0 | The bottom coating layer being not peeled off. | The pattern being brilliant, clear, fine, and vivid. |
| | Compound 5 | Level 0 | The bottom coating layer being not peeled off. | The pattern being brilliant, clear, fine, and vivid. |

TABLE 3-continued

Test results of yellow ink

| Example/Comparative Example | Compound | Adherence | Deep-layer curing degree | Pattern effect |
|---|---|---|---|---|
| | Compound 9 | Level 0 | The bottom coating layer being not peeled off. | The pattern being brilliant, clear, fine, and vivid. |
| | Compound 14 | Level 0 | The bottom coating layer being not peeled off. | The pattern being brilliant, clear, fine, and vivid. |
| | Compound 24 | Level 0 | The bottom coating layer being not peeled off. | The pattern being brilliant, clear, fine, and vivid. |
| | Compound 34 | Level 0 | The bottom coating layer being not peeled off. | The pattern being brilliant, clear, fine, and vivid. |
| | Compound 38 | Level 0 | The bottom coating layer being not peeled off. | The pattern being brilliant, clear, fine, and vivid. |
| | Compound 39 | Level 0 | The bottom coating layer being not peeled off. | The pattern being brilliant, clear, fine, and vivid. |
| | Compound 40 | Level 0 | The bottom coating layer being not peeled off. | The pattern being brilliant, clear, fine, and vivid. |
| | Compound 41 | Level 0 | The bottom coating layer being not peeled off. | The pattern being brilliant, clear, fine, and vivid. |
| | Compound 43 | Level 1 | The bottom coating layer being not peeled off. | The pattern being brilliant, clear, fine, and vivid. |
| | Compound 45 | Level 0 | The bottom coating layer being not peeled off. | The pattern being brilliant, clear, fine, and vivid. |
| | Compound 48 | Level 0 | The bottom coating layer being not peeled off. | The pattern being brilliant, clear, fine, and vivid. |
| | Compound 50 | Level 0 | The bottom coating layer being not peeled off. | The pattern being brilliant, clear, fine, and vivid. |
| | Compound 52 | Level 1 | The bottom coating layer being not peeled off. | The pattern being brilliant, clear, fine, and vivid. |
| | Compound 55 | Level 0 | The bottom coating layer being not peeled off. | The pattern being brilliant, clear, fine, and vivid. |
| | Compound 57 | Level 0 | The bottom coating layer being not peeled off. | The pattern being brilliant, clear, fine, and vivid. |
| Comparative Example | 369 | Level 2 | The bottom being soft and easily peelable off. | The edge of the pattern being unclear and easily peelable off. |
| | 907 | Level 2 | The bottom being soft and easily peelable off. | The bottom being incompletely cured. |

TABLE 4

Test results of red ink

| Example/Comparative Example | Compound | Adherence | Deep-layer curing degree | Pattern effect |
|---|---|---|---|---|
| Example | Compound 4 | Level 0 | The bottom coating layer being not peeled off. | The pattern being brilliant, clear, fine, and vivid. |
| | Compound 5 | Level 0 | The bottom coating layer being not peeled off. | The pattern being brilliant, clear, fine, and vivid. |
| | Compound 9 | Level 0 | The bottom coating layer being not peeled off. | The pattern being brilliant, clear, fine, and vivid. |
| | Compound 14 | Level 0 | The bottom coating layer being not peeled off. | The pattern being brilliant, clear, fine, and vivid. |
| | Compound 24 | Level 0 | The bottom coating layer being not peeled off. | The pattern being brilliant, clear, fine, and vivid. |

TABLE 4-continued

Test results of red ink

| Example/Comparative Example | Compound | Adherence | Deep-layer curing degree | Pattern effect |
|---|---|---|---|---|
| | Compound 34 | Level 0 | The bottom coating layer being not peeled off. | The pattern being brilliant, clear, fine, and vivid. |
| | Compound 38 | Level 0 | The bottom coating layer being not peeled off. | The pattern being brilliant, clear, fine, and vivid. |
| | Compound 40 | Level 0 | The bottom coating layer being not peeled off. | The pattern being brilliant, clear, fine, and vivid. |
| | Compound 41 | Level 1 | The bottom coating layer being not peeled off. | The pattern being brilliant, clear, fine, and vivid. |
| | Compound 43 | Level 1 | The bottom coating layer being not peeled off. | The pattern being brilliant, clear, fine, and vivid. |
| | Compound 45 | Level 0 | The bottom coating layer being not peeled off. | The pattern being brilliant, clear, fine, and vivid. |
| | Compound 48 | Level 0 | The bottom coating layer being not peeled off. | The pattern being brilliant, clear, fine, and vivid. |
| | Compound 50 | Level 0 | The bottom coating layer being not peeled off. | The pattern being brilliant, clear, fine, and vivid. |
| | Compound 52 | Level 1 | The bottom coating layer being not peeled off. | The pattern being brilliant, clear, fine, and vivid. |
| | Compound 53 | Level 1 | The bottom coating layer being not peeled off. | The pattern being brilliant, clear, fine, and vivid. |
| | Compound 55 | Level 1 | The bottom coating layer being not peeled off. | The pattern being brilliant, clear, fine, and vivid. |
| | Compound 57 | Level 0 | The bottom coating layer being not peeled off. | The pattern being brilliant, clear, fine, and vivid. |
| Comparative Example | 369 | Level 2 | The bottom being soft and easily peelable off. | The edge of the pattern being unclear and easily peelable off. |
| | 907 | Level 3 | The bottom being soft and easily peelable off. | The bottom being incompletely cured. |

TABLE 5

Test results of blue ink

| Sample source | Compound | Adherence | Deep-layer curing degree | Pattern effect |
|---|---|---|---|---|
| Example | Compound 4 | Level 0 | The bottom coating layer being not peeled off. | The pattern being brilliant, clear, fine, and vivid. |
| | Compound 5 | Level 0 | The bottom coating layer being not peeled off. | The pattern being brilliant, clear, fine, and vivid. |
| | Compound 9 | Level 0 | The bottom coating layer being not peeled off. | The pattern being brilliant, clear, fine, and vivid. |
| | Compound 14 | Level 0 | The bottom coating layer being not peeled off. | The pattern being brilliant, clear, fine, and vivid. |
| | Compound 24 | Level 0 | The bottom coating layer being not peeled off. | The pattern being brilliant, clear, fine, and vivid. |
| | Compound 38 | Level 0 | The bottom coating layer being not peeled off. | The pattern being brilliant, clear, fine, and vivid. |
| | Compound 39 | Level 0 | The bottom coating layer being not peeled off. | The pattern being brilliant, clear, fine, and vivid. |
| | Compound 40 | Level 0 | The bottom coating layer being not peeled off. | The pattern being brilliant, clear, fine, and vivid. |
| | Compound 41 | Level 0 | The bottom coating layer being not peeled off. | The pattern being brilliant, clear, fine, and vivid. |
| | Compound 43 | Level 0 | The bottom coating layer being not peeled off. | The pattern being brilliant, clear, fine, and vivid. |
| | Compound 45 | Level 0 | The bottom coating layer being not peeled off. | The pattern being brilliant, clear, fine, and vivid. |

TABLE 5-continued

Test results of blue ink

| Sample source | Compound | Adherence | Deep-layer curing degree | Pattern effect |
|---|---|---|---|---|
| | Compound 48 | Level 0 | The bottom coating layer being not peeled off. | The pattern being brilliant, clear, fine, and vivid. |
| | Compound 50 | Level 0 | The bottom coating layer being not peeled off. | The pattern being brilliant, clear, fine, and vivid. |
| | Compound 52 | Level 1 | The bottom coating layer being not peeled off. | The pattern being brilliant, clear, fine, and vivid. |
| | Compound 53 | Level 0 | The bottom coating layer being not peeled off. | The pattern being brilliant, clear, fine, and vivid. |
| | Compound 55 | Level 0 | The bottom coating layer being not peeled off. | The pattern being brilliant, clear, fine, and vivid. |
| Comparative Example | 369 | Level 2 | The bottom being soft and easily peelable off. | The edge of the pattern being unclear and easily peelable off. |
| | 907 | Level 2 | The bottom being soft and easily peelable off. | The bottom being incompletely cured. |

TABLE 6

Test results of black ink

| Example/ Comparative Example | Compound | Adherence | Deep-layer curing degree | Pattern effect |
|---|---|---|---|---|
| Example | Compound 4 | Level 0 | The bottom coating layer being not peeled off. | The pattern being brilliant, clear, fine, and vivid. |
| | Compound 5 | Level 0 | The bottom coating layer being not peeled off. | The pattern being brilliant, clear, fine, and vivid. |
| | Compound 9 | Level 0 | The bottom coating layer being not peeled off. | The pattern being brilliant, clear, fine, and vivid. |
| | Compound 14 | Level 0 | The bottom coating layer being not peeled off. | The pattern being brilliant, clear, fine, and vivid. |
| | Compound 24 | Level 0 | The bottom coating layer being not peeled off. | The pattern being brilliant, clear, fine, and vivid. |
| | Compound 34 | Level 0 | The bottom coating layer being not peeled off. | The pattern being brilliant, clear, fine, and vivid. |
| | Compound 38 | Level 0 | The bottom coating layer being not peeled off. | The pattern being brilliant, clear, fine, and vivid. |
| | Compound 40 | Level 0 | The bottom coating layer being not peeled off. | The pattern being brilliant, clear, fine, and vivid. |
| | Compound 41 | Level 1 | The bottom coating layer being not peeled off. | The pattern being brilliant, clear, fine, and vivid. |
| | Compound 43 | Level 1 | The bottom coating layer being not peeled off. | The pattern being brilliant, clear, fine, and vivid. |
| | Compound 45 | Level 0 | The bottom coating layer being not peeled off. | The pattern being brilliant, clear, fine, and vivid. |
| | Compound 48 | Level 1 | The bottom coating layer being not peeled off. | The pattern being brilliant, clear, fine, and vivid. |
| | Compound 50 | Level 0 | The bottom coating layer being not peeled off. | The pattern being brilliant, clear, fine, and vivid. |
| | Compound 52 | Level 1 | The bottom coating layer being not peeled off. | The pattern being brilliant, clear, fine, and vivid. |
| | Compound 54 | Level 1 | The bottom coating layer being not peeled off. | The pattern being brilliant, clear, fine, and vivid. |
| | Compound 56 | Level 1 | The bottom coating layer being not peeled off. | The pattern being brilliant, clear, fine, and vivid. |
| | Compound 57 | Level 0 | The bottom coating layer being not peeled off. | The pattern being brilliant, clear, fine, and vivid. |
| Comparative Example | 369 | Level 3 | The bottom being soft and easily peelable off. | The edge of the pattern being unclear and easily peelable off. |
| | 907 | Level 3 | The bottom being soft and easily peelable off. | The bottom being incompletely cured. |

As can be seen from Table 3, Table 4, Table 5, and Table 6, the alpha-aminoketone photoinitiator of the present invention containing a fluorene structure has a higher sensitivity, a better deep curing property in a colored system, and more excellent mechanical properties after a film is formed.

As can be seen from the description above, the following technical effects are achieved in the Examples of the present invention described above: the fluorenylaminoketone photoinitiator provided by the present invention can effectively improve the solubility of traditional photoinitiators and reduce the use of micromolecular active diluents, and also has high sensitivity and good effect of deep curing. It has very good promotion effect on popularization and application of colored ink systems in the field of photocuring.

Application systems of the UV photocurable composition containing a fluorenylaminoketone photoinitiator will be further elaborated in conjunction with specific Examples below. Methods and criteria for evaluation were as follows.

I. With respect to the developability, a pattern on a substrate was observed with a scanning electron microscope (SEM), wherein no residue was observed in unexposed portions (○); a small amount of residue was observed in unexposed portions, but the residual amount was acceptable (◎); and significant residue was observed in unexposed portions (●); and with respect to the pattern integrity, it depended on observation of the presence of defects in a pattern, wherein there was no defect (△); there were a few defects (□); and there were severe defects (▲);

II. With respect to the residual odor of a cured film, it was evaluated by smelling with the nose, wherein test results were divided into three levels which were 1 (odorless), 2 (odorous), and 3 (irritatingly odorous).

III. With respect to the yellowing, it was evaluated by the value of Δb which was read by full transmission scan with a scan wavelength of 400-700 nm by using a colorimeter (X-Rite Color i7, United States), wherein the smaller Δb was, the less significant the yellowing was; and conversely, the greater Δb was, the more severe the yellowing was.

IV. With respect to the evaluation of the adhesion, the adhesion of a coating film was evaluated by a crosscut test method with reference to GB9286-88 "Paints and varnishes—Crosscut test for Films". According to the degree of damage, it was divided into 0-5 levels (6 levels in total), wherein level 0 was the best, and there was not any compartment which was peeled off the film surface; and level 5 was extremely bad, badly peeling occurring on the film surface.

In the discussion described below, the components were calculated in weight percent in the formulation of the UV photocurable composition, and Irgacure 907 and APi-307 were used as referential example compounds under the same conditions.

Here, structural formulae of 907 and 307 were as shown below:

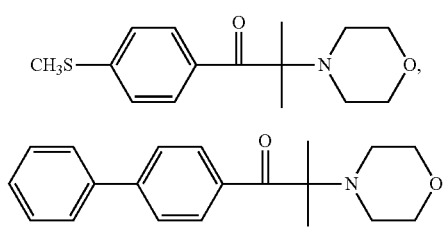

907

307

Example 21: UV Coating

| Material name | Usage amount (part by mass) |
|---|---|
| Aromatic acrylate hemiester | 46 |
| Low-viscosity aromatic monoacrylate | 22 |
| POEA (phenoxyethyl acrylate) | 20 |
| Carbon black (Raven 450) | 4.0 |
| Photoinitiator | 4.5 |
| ITX | 0.5 |
| BP (benzophenone) | 2.0 |
| Leveling agent | 1.0 |

Coating conditions: with reference to "GB/T 9271-2008 Paints and varnishes—Standards panels for testing", a substrate, which was a tin-plated steel plate, was subjected to pretreatment, and then a formulation, which was uniformly stirred in a dark room, was coated on the tin-plated steel plate with a 25 #wire bar, wherein the coating layer had a thickness of approximately 25 μm; exposure conditions: a RW-UV.70201 track type exposure machine was used and the radiation wavelength was 250-450 nm; aging conditions: after exposure, baking was performed in an oven at 80° C. for 24 h, and test results were as shown in Table 7 below:

TABLE 7

| | | Exposure demand mJ/cm² | Yellowing | Odor | Adherence |
|---|---|---|---|---|---|
| The present invention | Compound 4 | 120 | 0.72 | 1 | Level 0 |
| | Compound 5 | 110 | 0.74 | 1 | Level 0 |
| | Compound 9 | 130 | 0.68 | 1 | Level 0 |
| | Compound 14 | 110 | 0.74 | 1 | Level 0 |
| | Compound 24 | 120 | 0.77 | 1 | Level 0 |
| | Compound 26 | 110 | 0.79 | 1 | Level 0 |
| | Compound 28 | 110 | 0.70 | 1 | Level 0 |
| | Compound 32 | 110 | 0.68 | 1 | Level 0 |
| | Compound 34 | 110 | 0.75 | 1 | Level 0 |
| | Compound 38 | 110 | 0.68 | 1 | Level 0 |
| | Compound 45 | 120 | 0.73 | 1 | Level 0 |
| | Compound 48 | 110 | 0.71 | 1 | Level 0 |
| | Compound 50 | 120 | 0.75 | 1 | Level 0 |
| | Compound 52 | 120 | 0.69 | 1 | Level 0 |
| | Compound 57 | 110 | 0.73 | 1 | Level 0 |
| Comparative Example | 907 | 200 | 2.68 | 3 | Level 1 |
| | 307 | 220 | 1.33 | 1 | Level 1 |

Example 22: UV Etching Resist Ink

| Material name | Usage amount (part by mass) |
|---|---|
| Aromatic acid methacrylate hemiester SB400 | 55 |
| TMPTA (trimethylolpropane triacrylate) | 25 |
| Photoinitiator | 3 |
| ITX | 1.5 |
| Phthalocyanine blue | 1 |
| Talc powder | 14 |
| Leveling agent | 0.5 |

Printing conditions: a 100T screen was used, and the dry film thickness was 8-10 μm; baking conditions: baking was performed at 75° C. for 20 minutes; exposure conditions: a RW-UV.70201 track type exposure machine was used and the radiation wavelength was 250-450 nm; development conditions: 1% sodium carbonate solution was used, and development was performed at 30±2° C. for 40s, and test results were as shown in Table 8 below:

TABLE 8

|  |  | Exposure demand mJ/cm² | Developability | Pattern integrity | Yellowing | Odor |
|---|---|---|---|---|---|---|
| The present invention | Compound 3 | 110 | ○ | Δ | 0.72 | 1 |
|  | Compound 5 | 100 | ○ | Δ | 0.66 | 1 |
|  | Compound 10 | 110 | ○ | Δ | 0.68 | 1 |
|  | Compound 15 | 90 | ○ | Δ | 0.65 | 1 |
|  | Compound 24 | 100 | ○ | Δ | 0.68 | 1 |
|  | Compound 27 | 110 | ○ | Δ | 0.63 | 1 |
|  | Compound 29 | 110 | ○ | Δ | 0.70 | 1 |
|  | Compound 31 | 100 | ○ | Δ | 0.71 | 1 |
|  | Compound 35 | 100 | ○ | Δ | 0.75 | 1 |
|  | Compound 37 | 100 | ○ | Δ | 0.68 | 1 |
|  | Compound 39 | 110 | ○ | Δ | 0.75 | 1 |
|  | Compound 42 | 100 | ○ | Δ | 0.72 | 1 |
|  | Compound 43 | 110 | ○ | Δ | 0.69 | 1 |
|  | Compound 45 | 110 | ○ | Δ | 0.62 | 1 |
|  | Compound 53 | 110 | ○ | Δ | 0.65 | 1 |
| Comparative Example | 907 | 160 | ○ | ▲ | 2.54 | 3 |
|  | 307 | 180 | ○ | ▲ | 1.28 | 1 |

Example 23: UV Solder Resist Ink

| Materials of composition A | Usage amount (part by mass) |
|---|---|
| Epoxy acrylic resin CN144 | 45 |
| DPHA (dipentaerythritol hexaacrylate) | 25 |
| Photoinitiator | 3 |
| 2-Ethylanthracene-9,10-diethyl ester | 0.5 |
| ITX | 1 |
| Phthalocyanine blue | 1 |
| Silica R972 | 1.5 |
| Precipitated barium sulfate | 22 |
| Defoamer | 1 |

| Materials of composition B | Usage amount |
|---|---|
| Epoxy acrylic resin CN2100 | 45 |
| DPHA | 30 |
| Silica R972 | 1.5 |
| Precipitated barium sulfate | 23 |
| Defoamer | 0.5 |

The composition A and the composition B were uniformly mixed at a ratio of 3:1, and placed for half an hour. Printing conditions: 36-43T screen printing was performed, and the dry film thickness was 12-15 μm; pre-baking conditions: the first surface was pre-baked for 20 minutes and the second surface was pre-baked for 25 minutes, at 75° C.; exposure conditions: a RW-UV.70201 track type exposure machine was used and the radiation wavelength was 250-450 nm; development conditions: 0.5% sodium hydroxide solution was used, and development was performed at 30±2° C. for 60s, and test results were as shown in Table 9 below:

TABLE 9

|  |  | Exposure demand mJ/cm² | Developability | Pattern integrity | Yellowing | Odor |
|---|---|---|---|---|---|---|
| The present invention | Compound 4 | 100 | ○ | Δ | 0.78 | 1 |
|  | Compound 5 | 90 | ○ | Δ | 0.76 | 1 |
|  | Compound 10 | 100 | ○ | Δ | 0.75 | 1 |
|  | Compound 15 | 90 | ○ | Δ | 0.78 | 1 |
|  | Compound 25 | 100 | ○ | Δ | 0.81 | 1 |
|  | Compound 26 | 110 | ○ | Δ | 0.79 | 1 |
|  | Compound 29 | 100 | ○ | Δ | 0.73 | 1 |
|  | Compound 30 | 110 | ○ | Δ | 0.76 | 1 |
|  | Compound 34 | 100 | ○ | Δ | 0.79 | 1 |
|  | Compound 38 | 100 | ○ | Δ | 0.75 | 1 |
|  | Compound 42 | 110 | ○ | Δ | 0.72 | 1 |
|  | Compound 45 | 100 | ○ | Δ | 0.74 | 1 |
|  | Compound 48 | 110 | ○ | Δ | 0.73 | 1 |
|  | Compound 54 | 100 | ○ | Δ | 0.75 | 1 |
| Comparative Example | 907 | 180 | ○ | ▲ | 2.54 | 3 |
|  | 307 | 190 | ◉ | ▲ | 1.03 | 1 |

Example 24: UV Flexographic Printing Ink

| Material name | Usage amount (part by mass) |
|---|---|
| Polyester acrylic resin EB657 | 10 |
| Epoxy acrylic resin | 5 |
| 3-Propoxylated glycerol triacrylate | 30 |
| TPGDA (tripropylene glycol diacrylate) | 31 |
| Photoinitiator | 2 |
| ITX (isopropythioxanthone) | 2 |
| EDAB | 3 |
| Stabilizer | 1.5 |
| Pigment PY13 | 14 |
| Dispersant | 1.5 |

The above raw materials were uniformly mixed in a dark room and applied in a thickness of 5 μm onto a white paperboard. Exposure conditions: a RW-UV.70201 track type exposure machine was used, and the radiation wavelength was 250-450 nm; and test results were as shown in Table 10 below:

TABLE 10

| | | Exposure demand mJ/cm$^2$ | Yellowing | Odor | Adherence |
|---|---|---|---|---|---|
| The present invention | Compound 3 | 100 | 0.56 | 1 | Level 0 |
| | Compound 6 | 90 | 0.62 | 1 | Level 0 |
| | Compound 10 | 100 | 0.66 | 1 | Level 0 |
| | Compound 16 | 110 | 0.61 | 1 | Level 0 |
| | Compound 25 | 100 | 0.63 | 1 | Level 0 |
| | Compound 26 | 100 | 0.59 | 1 | Level 0 |
| | Compound 29 | 100 | 0.59 | 1 | Level 0 |
| | Compound 33 | 100 | 0.62 | 1 | Level 0 |
| | Compound 34 | 90 | 0.65 | 1 | Level 0 |
| | Compound 36 | 90 | 0.62 | 1 | Level 0 |
| | Compound 42 | 100 | 0.66 | 1 | Level 0 |
| | Compound 44 | 110 | 0.61 | 1 | Level 0 |
| | Compound 51 | 100 | 0.58 | 1 | Level 0 |
| | Compound 54 | 110 | 0.63 | 1 | Level 0 |
| Comparative Example | 907 | 170 | 2.56 | 3 | Level 1 |
| | 307 | 180 | 0.98 | 1 | Level 1 |

Example 25: UV Offset Printing Ink

| Material name | Usage amount (part by mass) |
|---|---|
| Epoxy acrylic resin CN2204 | 40 |
| Tetrafunctional urethane acrylate CN294 | 16 |
| Hexafunctional urethane acrylate CN293 | 12 |
| Pigment carbon black | 18 |
| Talc powder | 4 |
| Active amine CN373 | 5 |
| Photoinitiator | 5 |

The above raw materials were uniformly mixed in a dark room and applied onto a plastic substrate in a thickness of 2 μm. Exposure conditions: a RW-UV.70201 track type exposure machine was used, and the radiation wavelength was 250-450 nm; and test results were as shown in Table 11 below:

TABLE 11

| | | Exposure demand mJ/cm$^2$ | Yellowing | Odor | Adherence |
|---|---|---|---|---|---|
| The present invention | Compound 3 | 120 | 0.63 | 1 | Level 0 |
| | Compound 7 | 110 | 0.58 | 1 | Level 0 |
| | Compound 9 | 110 | 0.66 | 1 | Level 0 |
| | Compound 14 | 110 | 0.68 | 1 | Level 0 |
| | Compound 24 | 110 | 0.58 | 1 | Level 0 |
| | Compound 27 | 110 | 0.59 | 1 | Level 0 |
| | Compound 30 | 120 | 0.68 | 1 | Level 0 |
| | Compound 33 | 110 | 0.62 | 1 | Level 0 |
| | Compound 35 | 100 | 0.70 | 1 | Level 0 |
| | Compound 38 | 110 | 0.65 | 1 | Level 0 |
| | Compound 41 | 100 | 0.64 | 1 | Level 0 |
| | Compound 43 | 110 | 0.70 | 1 | Level 0 |
| | Compound 48 | 100 | 0.63 | 1 | Level 0 |
| | Compound 50 | 100 | 0.62 | 1 | Level 0 |
| Comparative Example | 907 | 200 | 2.34 | 3 | Level 1 |
| | 369 | 210 | 1.08 | 1 | Level 1 |

As can be seen from experimental results of Examples 21-25, the photocurable composition of the present invention containing a fluorenylaminoketone photoinitiator is used in photocurable coatings ands, and has advantages of good photocuring property, good yellowing resistance, no residual odor after curing, and excellent overall properties.

Those described above are merely preferred Examples of the present invention, and are not intended to limit the present invention. With respect to the person skilled in the art, there may be various modifications and variations of the present invention. All of modifications, equivalent replacements, improvements, and the like, which are within the spirit and the principle of the present invention, should be encompassed in the scope protected by the present invention.

What is claimed is:

1. A fluorenylaminoketone photoinitiator, wherein the photoinitiator comprises a compound having a structure represented by general formula (I) or a derivative compound thereof,

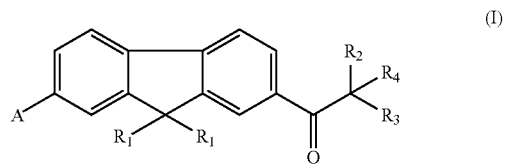

wherein,
A represents hydrogen, a halogen, a nitro group, a $C_1$-$C_{20}$ linear or branched alkyl group, a $C_3$-$C_{10}$ alkylcycloalkyl group, a $C_4$-$C_{10}$ cycloalkylalkyl group,

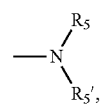

—$COR_6$, or a —CO—$CR_2R_3R_4$ group, wherein, optionally, —$CH_2$— is substituted with O, N, S, or C(=O);
$R_1$ represents hydrogen, a halogen, a $C_1$-$C_{20}$ linear or branched alkyl group, a $C_4$-$C_{20}$ cycloalkylalkyl group, or a $C_2$-$C_{20}$ alkenyl group, wherein, optionally, —CH$_2$— in R$_1$ is substituted with O, N, S, or C(=O), and, optionally, a ring is formed between R$_1$s;

R$_2$ and R$_3$ each independently represent a C$_1$-C$_{20}$ linear or branched alkyl group, a C$_3$-C$_{20}$ cycloalkyl group, a C$_4$-C$_{20}$ cycloalkylalkyl group, a C$_4$-C$_{20}$ alkylcycloalkyl group, a C$_6$-C$_{20}$ aryl group, or a C$_6$-C$_{20}$ alkylaryl group, wherein, optionally, one or more hydrogen atoms in these groups is each independently substituted with an alkyl group, a halogen, a hydroxy group, or a nitro group, and optionally, —CH$_2$— in R$_2$ and R$_3$ is substituted with O, N, S, or C(=O), and, optionally, R$_2$ and R$_3$ is linked to each other to form a ring;

or R$_2$ represents a C$_1$-C$_{20}$ linear or branched alkyl group or a C$_2$-C$_{20}$ alkenyl group, and R$_3$ is selected from any one of the following groups:

a) a group having a chemical formula as follows:

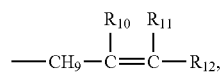

wherein R$_9$ represents hydrogen, a C$_1$-C$_8$ alkyl group, or a phenyl group, and R$_{10}$, R$_{11}$, and R$_{12}$ each independently represent hydrogen or a C$_1$-C$_4$ alkyl group; or b) a group having a chemical formula as follows:

wherein n is 0, 1, 2, or 3; or c) a group having a chemical formula as follows:

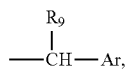

wherein Ar is a substituted or unsubstituted phenyl, naphthyl, furanyl, thienyl, or pyridinyl group;

R$_4$ represents a a N-piperidinyl group, or a N-pyrrolyl group, wherein, optionally, one or more hydrogen atoms in these groups is substituted with a halogen or a hydroxy group;

R$_5$ and R$_5$' each independently represent a C$_1$-C$_{20}$ linear or branched alkyl group, a C$_4$-C$_{20}$ cycloalkyl group, a C$_2$-C$_{20}$ alkenyl group, a C$_6$-C$_{20}$ aryl group, or a C$_6$-C$_{20}$ alkylaryl group, wherein, optionally, one or more hydrogen atoms in these groups is each independently substituted with an alkyl group, a halogen, a hydroxy group, or a nitro group, and optionally, —CH$_2$— in these groups is substituted with —O—;

or, optionally, R$_5$ and R$_5$' forms a five-membered or six-membered ring by being linked to each other or via —O—, —S—, or —NH—;

R$_6$ represents a C$_1$-C$_{20}$ linear or branched alkyl group, a C$_4$-C$_{20}$ cycloalkyl group, a C$_4$-C$_{20}$ alkylcycloalkyl group, a C$_2$-C$_{20}$ alkenyl group, a C$_6$-C$_{20}$ aryl group, or a C$_6$-C$_{20}$ alkylaryl group, wherein, optionally, —CH$_2$— in these groups is substituted with —O— or —S—, and, optionally, one or more hydrogen atoms in these groups is independently substituted with a group selected from an alkyl group, a halogen, a nitro group, a cyano group, SR$_7$, and OR$_8$;

R$_7$ and R$_8$ each independently represent hydrogen or a C$_1$-C$_{20}$ linear or branched alkyl group.

2. The fluorenylaminoketone photoinitiator according to claim 1, comprising a derivative compound of the photoinitiator having a structure represented by general formula (I) and wherein the derivative compound of the photoinitiator having a structure represented by general formula (I) comprises derivative compounds obtained by maintaining a main structure of a compound of formula (I) unchanged while allowing one or more branch chain(s) thereof to be substituted or linked to each other.

3. The fluorenylaminoketone photoinitiator according to claim 2, comprising a derivative compound of the photoinitiator having a structure represented by general formula (I) and wherein the derivative compound is a compound having a structure represented by general formula (II) or (III):

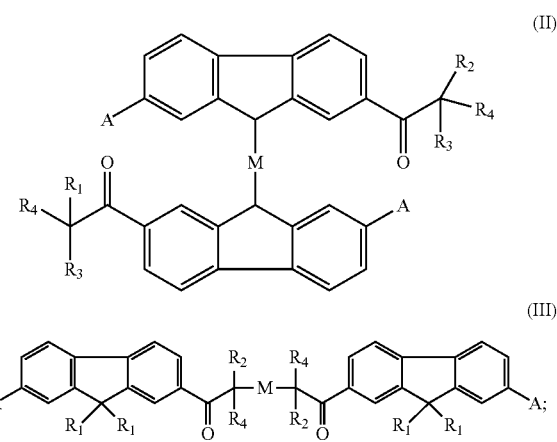

wherein M represents a linking group formed by dimerization and, optionally, is absent, a C$_1$-C$_{10}$ linear or branched alkylene group, or a C$_6$-C$_{12}$ arylene or heteroarylene group, and optionally, —CH$_2$— in M is substituted with sulfur, oxygen, NH, or a carbonyl group, and optionally, a hydrogen atom is substituted with OH or NO$_2$.

4. A UV photocurable composition comprising: an olefinically unsaturated photopolymerizable compound and a photoinitiator; wherein the photoinitiator is the fluorenylaminoketone photoinitiator as claimed in claim 1.

5. The UV photocurable composition according to claim 4, wherein the photoinitiator comprising a photoinitiator having a structure represented by general formula (I) or the derivative compound thereof is a mixture of two or more of the compounds.

6. The UV photocurable composition according to claim 4, wherein the olefinically unsaturated photopolymerizable compound is a compound comprising one carbon-carbon double bond; or the olefinically unsaturated photopolymerizable compound is a compound comprising two or more carbon-carbon double bonds.

7. The UV photocurable composition according to claim 4, wherein the UV photocurable composition is used as a UV etching resist ink or a UV solder resist ink, and at least one compound of the olefinically unsaturated photopolymerizable compounds used contains a carboxyl-containing resin.

8. The UV photocurable composition according to claim 7, wherein the carboxyl-containing resin is a (meth)acrylate, an ethylenically unsaturated carboxylic acid, or a (meth)acrylate-based polymer.

9. The UV photocurable composition according to claim 4, wherein the UV photocurable composition further comprises another photoinitiator, which is one or more selected from the group consisting of benzophenone, benzildimethyl ketal, 2-hydroxy-2-methyl-1-phenyl-acetone, 1-hydroxy-cyclohexyl-phenyl-one, isopropylthioxanthene, (2,4,6-trimethyl-benzoyl)diphenyphosphine oxide, and bis(2,4,6-trimethyl benzoyl)-phenylphosphine oxide.

10. The UV photocurable composition according to claim 4, wherein the UV photocurable composition further comprises a sensitizer.

11. The UV photocurable composition according to claim 4, wherein the UV photocurable composition further comprises a colorant, which is an inorganic pigment or an organic pigment.

12. The UV photocurable composition according to claim 4, wherein the UV photocurable composition further comprises an additive, which includes one or more selected from: a surfactant, a wetting agent, a dispersant, a rheology modifier, a defoamer, or a storage enhancer.

13. A preparation method of the fluorenylaminoketone photoinitiator as claimed in claim 1, the preparation method comprising:

(1) subjecting a raw material a and a raw material b to a Friedel-Crafts reaction to generate an intermediate a with a reaction formula as follows:

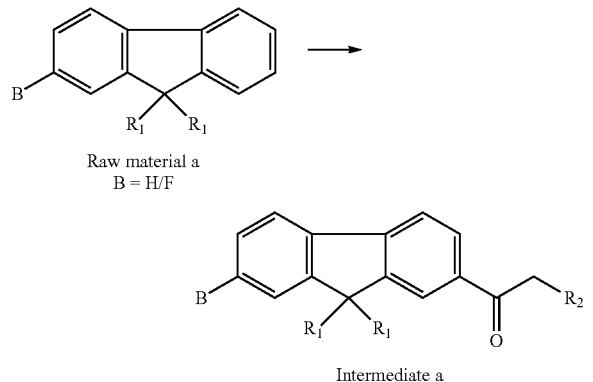

Raw material a
B = H/F

Intermediate a (2) subjecting the intermediate a to a substitution reaction to generate an intermediate b:

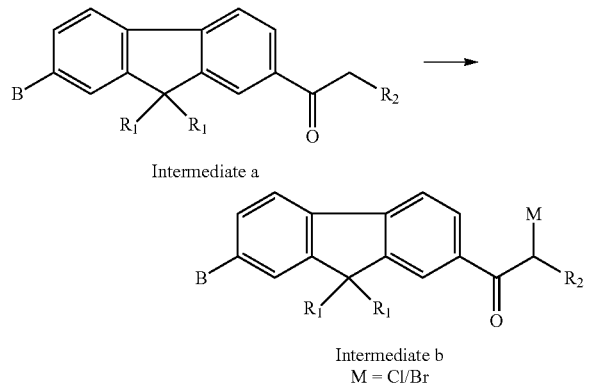

Intermediate a

Intermediate b
M = Cl/Br (3) subjecting the intermediate b to a substitution reaction to generate an intermediate c:

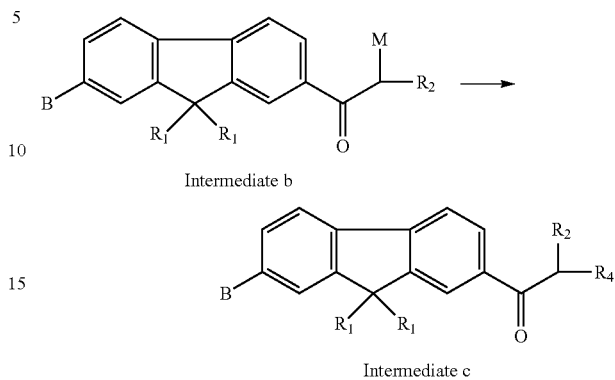

Intermediate b

Intermediate c (4) subjecting the intermediate c to a Stevens rearrangement reaction to generate an intermediate d:

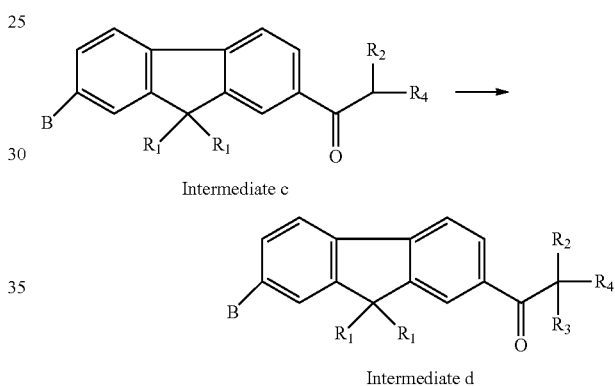

Intermediate c

Intermediate d (5) if a product in which A=H is expected to be obtained, then B=H in the raw material a, and the intermediate d is a compound of general formula (I);

if a product in which

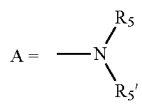

$$A = -N\begin{matrix}R_5\\R_5'\end{matrix}$$

is expected to be obtained, then B=F in the raw material a, subjecting the intermediate d to substitution reaction to generate a compound having general formula (I) as follows;

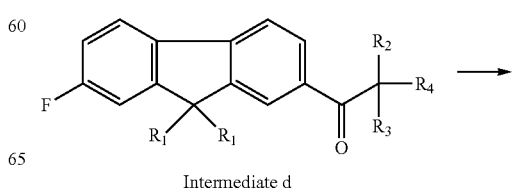

Intermediate d

-continued

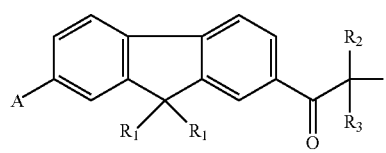

Formula (I)

if a product in which

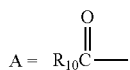

is expected to be obtained, then B=H in the raw material a, subjecting the intermediated to a Friedel-Crafts reaction to generate a compound having general formula (I) as follows;

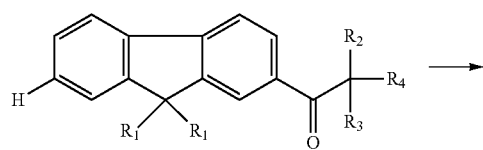

Intermediate d

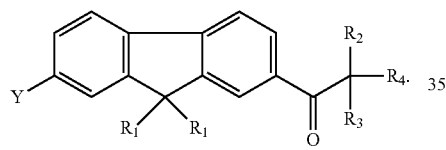

Formula (I)

14. A fluorenylaminoketone photoinitiator that comprises one or more compounds represented by the following:

Compound 1

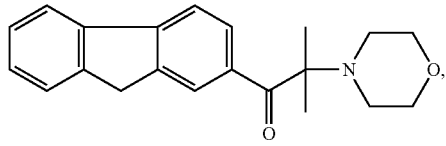

Compound 2

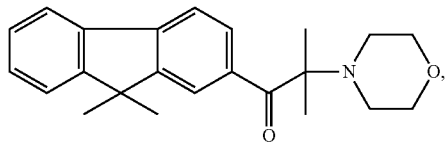

Compound 3

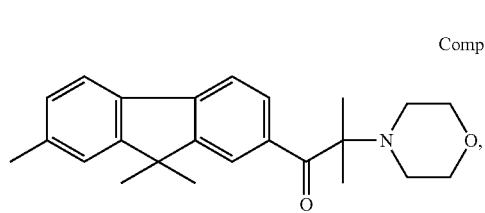

Compound 4

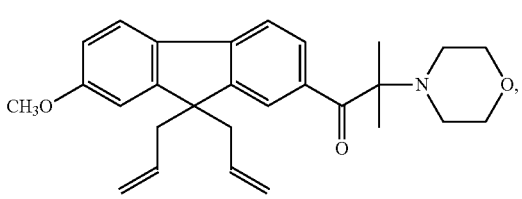

Compound 5

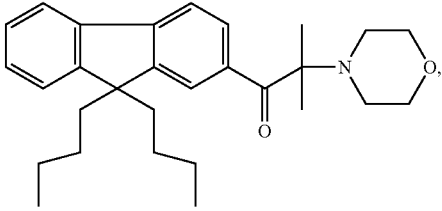

Compound 6

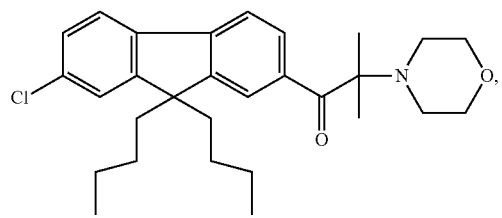

Compound 7

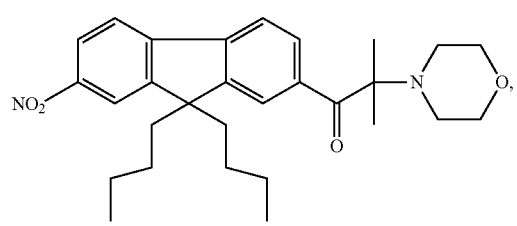

Compound 8

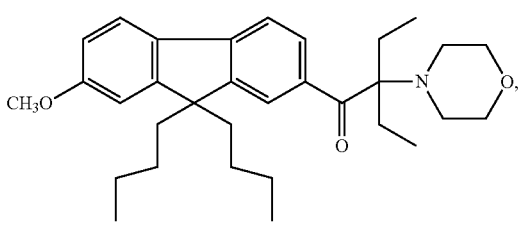

Compound 9

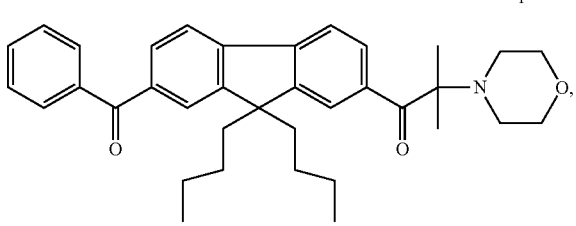

Compound 10

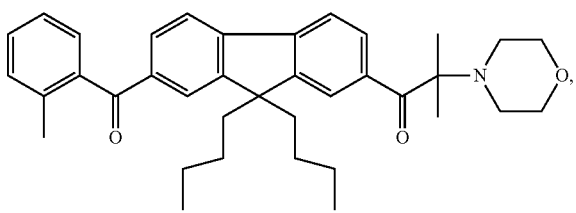

Compound 11
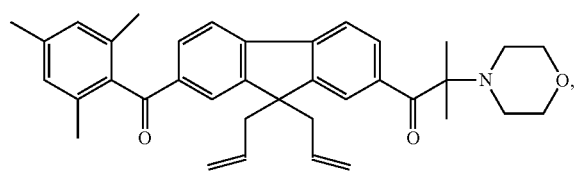
Compound 12
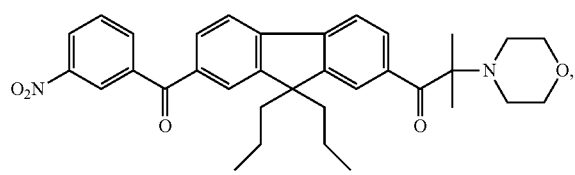
Compound 15
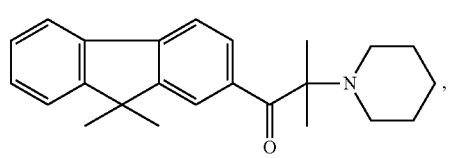
Compound 16
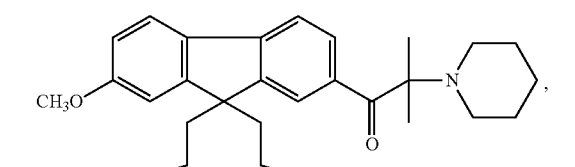
Compound 17
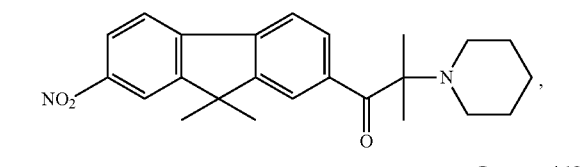
Compound 18
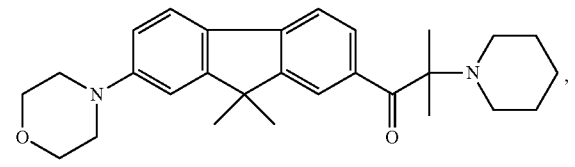
Compound 19
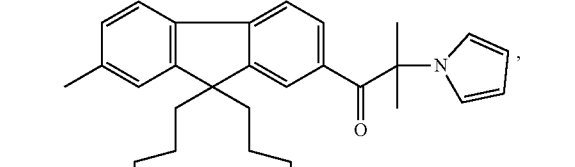
Compound 22
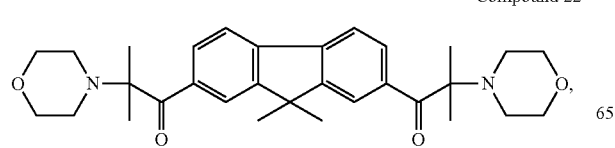
Compound 23
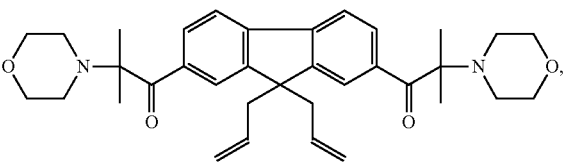
Compound 24
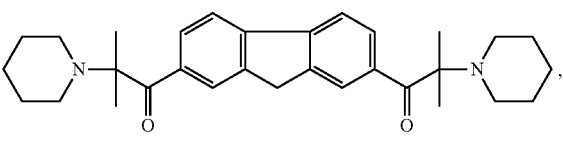
Compound 28
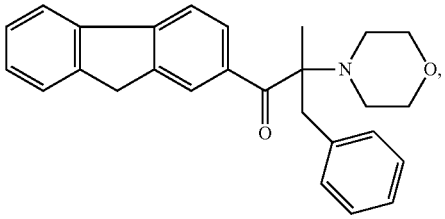
Compound 29
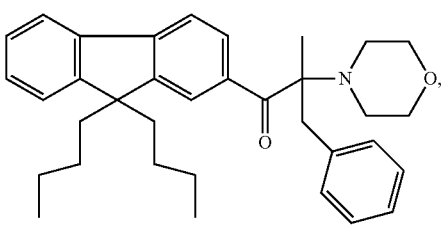
Compound 32
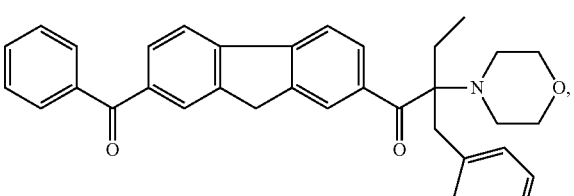
Compound 33
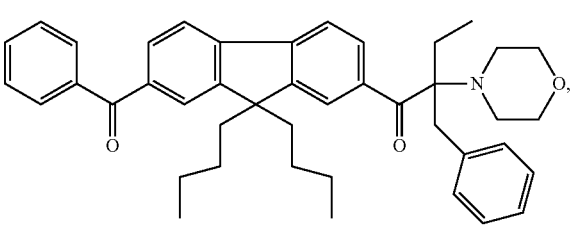
Compound 35
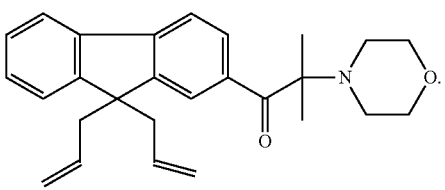

15. A fluorenylaminoketone photoinitiator that comprises:

Compound 36

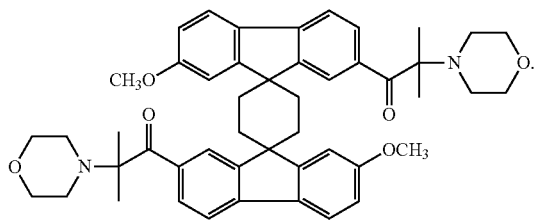

16. The UV photocurable composition according to claim 4, comprising a derivative compound of the photoinitiator having a structure represented by general formula (I) and wherein the derivative compound of the photoinitiator having a structure represented by general formula (I) comprises derivative compounds obtained by maintaining a main structure of a compound of formula (I) unchanged while allowing branch chain(s) thereof to be substituted or linked to each other.

17. The UV photocurable composition according to claim 4, comprising a derivative compound of the photoinitiator having a structure represented by general formula (I) and wherein the derivative compound is a compound having a structure represented by general formula (II) or (III):

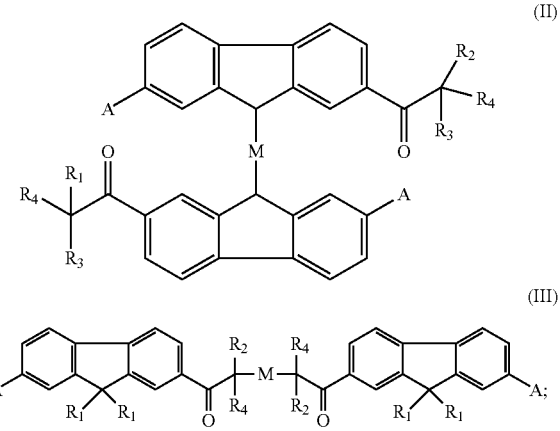

wherein M represents a linking group formed by dimerization and, optionally, is absent, a $C_1$-$C_{10}$ linear or branched alkylene group, or a $C_6$-$C_{12}$ arylene or heteroarylene group, and optionally, —$CH_2$— in M is substituted with sulfur, oxygen, NH, or a carbonyl group, and optionally, a hydrogen atom is substituted with OH or $NO_2$.

18. The preparation method according to claim 13, comprising preparing a derivative compound of the photoinitiator having a structure represented by general formula (I), wherein the derivative compound of the photoinitiator having a structure represented by general formula (I) comprises derivative compounds obtained by maintaining a main structure of a compound of formula (I) unchanged while allowing one or more branch chain(s) thereof to be substituted or linked to each other.

19. The preparation method according to claim 13, comprising preparing a derivative compound of the photoinitiator having a structure represented by general formula (I), wherein the derivative compound is a compound having a structure represented by general formula (II) or (III):

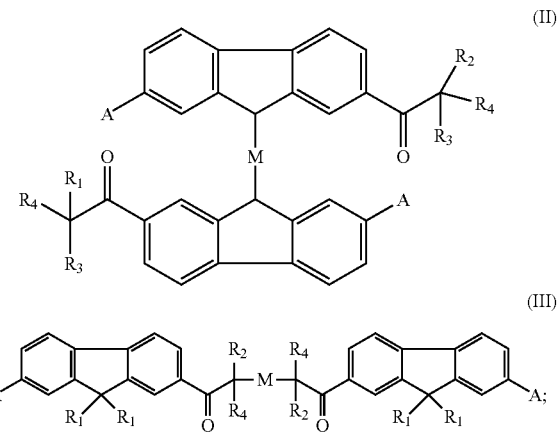

wherein M represents a linking group formed by dimerization and, optionally, is absent, a $C_1$-$C_{10}$ linear or branched alkylene group, or a $C_6$-$C_{12}$ arylene or heteroarylene group, and optionally, —$CH_2$— in M is substituted with sulfur, oxygen, NH, or a carbonyl group, and optionally, a hydrogen atom is substituted with OH or $NO_2$.

* * * * *

UNITED STATES PATENT AND TRADEMARK OFFICE
CERTIFICATE OF CORRECTION

PATENT NO. : 11,118,065 B2
APPLICATION NO. : 16/485724
DATED : September 14, 2021
INVENTOR(S) : Xiaochun Qian Page 1 of 1

It is certified that error appears in the above-identified patent and that said Letters Patent is hereby corrected as shown below:

On the Title Page

Item (73): should be corrected to read:
(73) Assignee: CHANGZHOU TRONLY ADVANCED ELECTRONIC MATERIALS CO., LTD., Jiangsu (CN) and CHANGZHOU TRONLY NEW ELECTRONIC MATERIALS CO., LTD., Jiangsu (CN)

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*